United States Patent [19]
Hoffman et al.

[11] Patent Number: 5,661,124
[45] Date of Patent: *Aug. 26, 1997

[54] BLOOD SUBSTITUTES

[75] Inventors: Stephen J. Hoffman, Denver, Colo.; Kiyoshi Nagai, Cambridge, England

[73] Assignee: Somatogen, Inc., Boulder, Colo.

[*] Notice: The term of this patent shall not extend beyond the expiration date of Pat. No. 5,028,588.

[21] Appl. No.: 396,866

[22] Filed: Mar. 1, 1995

Related U.S. Application Data

[63] Continuation of Ser. No. 62,780, May 17, 1993, abandoned, which is a continuation of Ser. No. 443,950, Dec. 1, 1989, abandoned, which is a continuation-in-part of Ser. No. 194,338, May 16, 1988, Pat. No. 5,028,588.

[30] Foreign Application Priority Data

May 16, 1987 [GB] United Kingdom .................... 8711614

[51] Int. Cl.$^6$ .................... A61K 38/16; C07K 14/00
[52] U.S. Cl. .................... 514/6; 514/23; 514/832; 514/833; 530/385
[58] Field of Search .................... 424/529; 514/2, 514/4, 23, 6; 530/385

[56] References Cited

U.S. PATENT DOCUMENTS

| | | | |
|---|---|---|---|
| 3,928,574 | 12/1975 | Phillips | 424/679 |
| 4,301,144 | 11/1981 | Iwashita | 424/78 |
| 4,321,259 | 3/1982 | Nicolau | 424/101 |
| 4,336,248 | 6/1982 | Bonhard | 424/101 |
| 4,377,512 | 3/1983 | Ajusaka | 424/101 |
| 4,412,989 | 11/1983 | Iwashita | 424/177 |
| 4,473,563 | 9/1984 | Nicolau | 424/224 |
| 4,584,130 | 4/1986 | Bucci et al. | 530/385 |
| 4,598,064 | 7/1986 | Walder | 514/6 |
| 4,600,531 | 7/1986 | Walder | 530/385 |
| 4,650,678 | 3/1987 | Wong | 514/6 |
| 4,670,417 | 6/1987 | Iwasaki | 514/6 |
| 4,710,488 | 12/1987 | Wong | 424/101 |
| 4,923,442 | 5/1990 | Segall et al. | 514/23 |
| 4,927,806 | 5/1990 | Kramer et al. | 514/2 |
| 5,028,588 | 7/1991 | Hoffman et al. | 514/6 |
| 5,082,831 | 1/1992 | Leaf et al. | 514/56 |
| 5,084,558 | 1/1992 | Rausch et al. | 530/385 |
| 5,114,932 | 5/1992 | Runge | 514/58 |
| 5,449,759 | 9/1995 | Hoffman et al. | 530/385 |

OTHER PUBLICATIONS

Bolin, R. and Devento, F. in R.B. Bolin, R.P. Geyer and G.J. Nemo (Eds) Advances in Blood Substitute Research (1983) Alan R. Liss, Inc., New York, NY.

Davis, J.E./Measurement of Colligative Properties/Clinical Chemistry Theory, Analysis, and Correlation/1984/Chapter 12/232–239/D. Ed. D. Ladig, R. Kasper.

Deardorff, D.L./Tonicity, Osmoticity, and Osmolality, and Osmolarity/A. Oslo Ed Remington's Pharmaceutical Sciences, Mack Publishing Company, Eaton, Pa/(1980)/p. 1405, Second Column, Lines 2–5.

Fermi & Perutz/Haemoglobin and Myoglobin/Atlas of Molecular Structures in Biology (1981) Entire Text/Clarendon Press/Oxford.

Bunn & Forget/Hemoglobin: Molecular, Genetic and Clinical Aspects (1986) Entire Text W.B. Saunders Company/Philadelphia.

Beretta A. et al./Haemoglobin Torino—α43 (CDI) Phenylalanine→ Valine/Nature/(1968)217, 1016–1018.

Rabiner, S.F./Evaluation of a Stroma–Free Hemoglobin Solution For Use as a Plasma Expander/Nature (1967), 126, 1127–1142.

Thornton, J.M./Disulphide Bridges in Globular Proteins J. Exp. Med./(1981), 151, 261–287/Academic Press Inc./London.

Nagai & Thogersen/Generation of β–Globin by Sequence–Specific Proteolysis of a Hybrid Protein Produced Inescherichia Coli/Nature/J. Mol. Biol./(1984) 309, 810–812.

Liebhaber, S.A. et al./Cloning and Complete Nucleotide Sequence of Human 5'–α–Globin Gene/PNAS/(1980), 77(12), 7054–7058.

Moo–Penn, W.F. et al./Hemoglobin Raleigh(β1 Valine→ Acetylalanine). Structural and Functional Characterization/Biochemistry/(1977), 16, 4872–4879.

Moo–Penn, W.F. et al/Hemoglobin Connecticut (β21(B3) ASP→Gly): A Hemoglobin Variant With Low Oxygen Affinity/American J. of Hematology/(1981)/11, 137–145.

Idelson, L.I. et al/New Unstable Haemoglobin (Hb Moscva, β24 (B4) Gly→ASP) Found in the in the USSR/Nature/ 1974, 249, 768–770.

Gacon, G. et al/Structural and Functional Studies of Hb Rothschild β37 (C3) TRP→ARG a New Variant of the $α_1β_2$Contact/FEBS Letters (1977), 82(2), 243–246.

Keeling, M.M. et al./Hemoglobin Louisville (β42 (CD1) PHE→LEU): an Unstable Variant Causing Mild Hemolytic Anemia/J. of Clinical Invest./(1971), 50, 2395–2402.

Ogata, K. et al./Hemoglobin Sendagi (β42 PHE→VAL): A New Unstable Hemoglobin Variant Having an Amino Acid Substitution at CD1 of the β–Chain/Hemoglobin/(1986), 10(5), 469–481.

Yeager, A.M. et al./Hemoglobin Cheverly: an Unstable Hemoglobin Associated with Chronic Mild Anemia/Pediatr. Res./(1983),17, 503–507.

Marinucci, M. et al/Hemoglobin Bologna ($α_1β_2$61 (E5) LYS→MET) An Abnormal Human Hemoglobin with Low Oxygen Affinity/Biochimica et Biophysica Acta/(1981), 668,209–215.

Garel, M.C. et al./Hemoglobin J Cairo: β65 (E9) LYS→ GLN, A New Hemoglobin Variant Discovered in an Egyptian Family/Biochimica et Biophysica Acta/(1976), 420, 97–104.

(List continued on next page.)

Primary Examiner—Vasu S. Jagannathan
Assistant Examiner—Christine Saoud
Attorney, Agent, or Firm—Henry P. Nowak; Theresa A. Brown

[57] ABSTRACT

The present invention provides blood substitutes comprised of recombinantly produced mutant hemoglobin having an osmolarity greater than 303 milliosmoles per liter and less than 800 milliosmoles per liter. Such hyperosmolar blood substitute additionally comprises a physiologically acceptable molecule less diffusible than dextrose.

10 Claims, 6 Drawing Sheets

OTHER PUBLICATIONS

Shih, D.T.-B. et al./Hemoglobin Chico [β66(E10)LYS→THR]A New Variant with Decreased Oxygen Affinity/Hemoglobin/(1987), 11(5), 453–464.

Steadman, J.H. et al./Idiopathic Heinz Body Anaemia: Hb–Bristol (β67 (E11) VAL→ASP)/British J. of Haematology/(1970), 18, 435–446.

Stamatoyannopoulos, G. et al./Physiologic Implications of a Hemoglobin with Decreased Oxygen Affinity (Hemoglobin Seattle)/The New Eng. J. of Med./(1969), 281(17),915–919.

Schneider, R.G. et al./Hb Mobile [$\alpha_2 \beta_2 73$(E17) ASP→VAL]: A New Variant/Biochemical Genetics/(1975), 13(7/8), 411–415.

Jones, R.T. et al./Hemoglobin Vancouver [$\alpha_2\beta_2 73$ (E17) ASP→TYR]: Its Structure and Function/J. of Molecular Evolution/(1976), 9, 37–44.

Sugihara, J. et al/Hemoglobin Rahere, A Human Hemoglobin Variant with Amino Acid Substitution at the 2,3–Diphosphoglycerate Binding Site/J. Clin. Invest./(1985), 76, 1169–1173.

Tatsis, B. et al/Hemoglobin Pyrgos$\alpha_2\beta_2^{83(EF7)GLY\to ASP}$: A New Hemoglobin Variant in Double Heterozygosity with Hemoglobin S/Blood/(1976), 47(5), 827–832.

Merault, G. et al/Hemoglobin Roseau–Pointe a Pitre $\alpha_2\beta_2 90$ (F6) GLU–GLY: A New Hemoglobin Variant with Slight Instability and Low Oxygen Affinity/FEBS Lett./(1985), 184(1), 10–13.

Nagel, R.L. et al/Hemoglobin Beth Israel, A Mutant Causing Clinically Apparent Cyanosis/N. England J. of Med./(1976), 295(3), 125–130.

Efremov, G.D. et al/Hemoglobin Richmond, A Human Hemoglobin Which Forms Asymmetric Hybrids with Other Hemoglobins/J. of Biol. Chem./(1969),244(22), 6105–6116.

Turner, J.W. et al./Characterization of Hemoglobin Burke [β107 (G9) GLY→ARG]/Biochem. Genetics/(1976), 14(7/8), 577–585.

Imamura, T. et al/Hemoglobin Yoshizuka (G10(108)β Asparagine→Aspartic Acid): A New Variant with a Reduced Oxygen Affinity from a Japanese Family/J.. Clin. Invest/ 1969,48,2341–2348.

Lawn, R.M. et al/The Nucleotide Sequence of the Human β Globin Gene/Cell/(1980),21,647–651.

Ahern, E. et al/Haemoglobin Caribbean β91 (F7) LEU→ARG: A Mildly Unstable Haemoglobin with a Low Oxygen Affinity/FEBS Letters/(1976), 69(1), 99–102.

Bratu, V. et al/Haemoglobin Bucuresti β42 (CDI) PHE→LEU, A Cause of Unstable Haemoglobin Haemoloytic Anaemia/Biochimica et Biophysica Acta/(1971), 251, 1–6.

Anderson, N.L. et al/Site of the Amino–Acid Substitution in Haemoglobin Seattle ($\alpha_2^A\beta_2^{76ASP}$)/Nature/(1973),243, 274–275.

Blouquit, Y. et al/Structural Study of Hemoglobin Hazebrouck, β38(C4) THR→PRO a New Abnormal Hemoglobin with Instability and Low Oxygen Affinity/FEBS Letts/ (1984),172(2), 155–158.

Dacie, J.V. et al/Haemoglobin Hammersmith (β42 (CDI) PHE→SER)/Nature/(1967), 216–663–665.

Schoner B./Recombinant DNA/Methods in Enzymology (1987), 153, 400–417/Edited by Ray Wu, Lawrence Grossman/Academic Press, Inc. San Diego.

Charache, S. et al/Hemoglobin Okaloosa (β48 (CD7) Leucine→Arginine) An Unstable Variant with Low Oxygen Affinity/J. of Clin. Invest./(1973), 52, 2858–2864.

Tait, R.C. et al/The Rapid Purification of T4 DNA Ligase from a λ T4 Lig Lysogen/J. of Bio. Chemistry/(1980)10, 813–815.

Boyer, P.D./Spectrophotometric Study of the Reaction of Protein Sulfhydryl Groups with Organic Mercurials/J. Am. Chem. Soc./(1954), 76,4331–4337.

Imai, K. et al/Studies on the Function of Abnormal Hemoglobins/Biochimica et Biophisica Acta/(1970), 200, 197–202.

Grantham, R. et al/Codon Catalog Usage is a Genome Strategy Modulated for Gene Expresivity/Nucleic Acids Research (1981),9(1), R43–R74.

Grunstein & Hogness/Colony Hybridization: A Method for the Isolation of Cloned DNAs That Contain a Specific Gene/PNAS–Biochemistry/(1975), 72(10), 3961–3965.

Wilson, J.T. et al/Insertion of Synthetic Copies of Human Globin Genes into Bacterial Plasmids/Nucleic Acids Research/(1978), 5(2), 563–581.

McCracken, A.A. et al/An Enrichment Selection for Mutants Resulting from Oligonucleotide–Directed Mutagenesis of Double–Stranded DNA/Biotechniques(1988), 6(4), 332–339.

MacDonald, V.W. et al/Coronary Vasoconstriction and Maintenance of Normal Myocardial Function with HPLC Purified Hemoglobin Ao and Pasteurized $\alpha$–$\alpha$ Cross Linked Hemoglobin/Faseb Journal/(1988), 2(6), Abstract 8217, p. A1711.

Bove, J.R./Transfusion–Transmitted Diseases: Current Problems and Challenges/Prog. in Hematology/(1986), 14 123–145.

Gait, M.J. et al/Rapid Synthesis of Oligodeoxyribonucleotides VII. Solid Phase Synthesis of Oligodeoxyribonucleotides by a Continuous Flow Phosphotriester Method on a Kieselguhr–Polyamide Support/Nucleic Acids Res./(1982), 10(20)6243–6254.

Lloyd, S. et al/Rapid Purification of Synthetic Oligonucleotides/Biotechniques/(1986) 4(1), 8–10.

Moo–Penn, W.F. et al/Hemoglobin Presbyterian: β108 (G10) Asparagine→Lysine, A Hemoglobin Variant with Low Oxygen Affinity/FEBS Letters/(1978), 92(1), 53–56.

Perutz, M.F./Regulation of Oxygen Affinity of Hemoglobin: Influence of Structure of the Globin on the Heme Iron/Ann. Rev. Biochem./(1979), 48, 327–86.

Feola, M. et al./Toxicity of Polymerized Hemoglobin Solutions/Surgery, Gynecology & Obstetrics/(1988), 166,211–222.

Sproat & Bannwarth/Improved Synthesis of Oligodeoxynucleotides on Controlled Pore Glass Using Phosphotriester Chemistry and a Flow System/Tetrahedron Let./(1983), 24(51),5771–5774.

Benson S.A./A Rapid Procedure For Isolation of DNA Fragments From Agarose Gels/Biotechniques/(1984), 2:66–67.

Benson & Taylor/A Rapid Small–Scale Procedure For Isolation of Phage λ DNA Biotechniques/(1984), 2:126–127.

Shaanan, B./Structure of Human Oxyhaemoglobin At 2.1 A Resolution/J. Mol. Biol./(1983), 171, 31–59.

Ohba, Y. et al/Hemoglobin Hirosaki ($\alpha$ 43 [CE 1] PHE→LEU), A New Unstable Variant/Biochimca et Biophysica Acta./(1975), 405, 155–160.

Knuth, A. et al/Hemoglobin Moabit: Alpha 86 (F7) LEU→ARG A New Unstable Abnormal Hemoglobin/Acta Haemat.(1979), 61, 121–124.

Wrightstone, R.N./Policies of the International Hemoglobin Information Center (IHIC) Hemoglobin/(1987), 11, 241–308.

Vieira & Messing/The pUC Plasmids, An M13mp 7–Derived System for Insertion Mutagenesis and Sequencing with Synthetic Universal Primers/Gene/(1982), 19, 259–268.

Nagai, K. et al/Distal Residues in the Oxygen Binding Site of Haemoglobin Studied by Protein Engineering/Nature/(1987), 329, 858–860.

Luisi & Nagai/Crystallographic Analysis of Mutant Human Haemoglobins Made–In Escherichia Coli/Nature/(1986), 320, 555–556.

Zoller & Smith/Oligonucleotide–Directed Mutagenesis of DNA Fragments Cloned Into M13 Vector/Methods in Enzymology/(1983), 100, 468–500/Academic Press.

King, M.A.R. et al/An Unstable Haemoglobin with Reduced Oxygen Affinity: Haemoglobin Peterborough, βIII (G13) Valine→Phenylalanine, Its Interaction with Normal Haemoglobin and with Haemoglobin Lepore/Brit. J. of Haematology/(1972), 22, 125–134.

Ranney, H.M. et al/Haemoglobin New York/Nature(1967), 213, 876–878.

Minnich, V. et al/Hemoglobin Hope: A Beta Chain Variant/Blood/(1965), 25(5), 830–838.

Ohba, Y. et al/HB Himeji or β140 (H18) ALA→ASP a Slightly Unstable Hemoglobin with Increased βN–Terminal Glycation/Hemoglobin/(1986), 10(2), 109–126.

Ward, J.W. et al/Transmission of Human Immunodeficiency Virus (HIV) by Blood Transfusions Screened as Negative for HIV Antibody/N. Eng. J. Med./(1988), 318(8), 473–478.

Imai, K./Measurement of Accurate Oxygen Equilibrium Curves by an Automatic Oxygenation Apparatus/Methods in Enzymology/(1981), 76, 438–449, Academic Press/NY.

Gill, S.J./Measurement of Oxygen Binding by Means of a Thin–Layer Optical Cell/Methods in Enzymology/(1981), 76, 427–438/Academic Press/NY.

Bonaventura & Riggs/Hemoglobin Kansas, A Human Hemoglobin with a Neutral Amino Acid Substitution and an Abnormal Oxygen Equilibrium/J. of Biol. Chem./(1968), 243(5), 980–901.

Sanger, F. et al/DNA Sequencing with Chain–Terminating Inhibitors/PNAS–Biochemistry/(1977), 74(12), 5463–5467.

Marotta, C.A. et al/Human β–Globin Messenger RNA/III. Nucleotide Sequences Derived from Complementary DNA/J. of Biological Chemistry(1977), 252(14), 5040–5051.

Nagai, K. et al/Oxygen Binding Properties of Human Mutant Hemoglobins Synthesized in Escherichia Coli/PNAS–Biochemistry/(1985), 7252–7255.

Stone A.M. et al/Renal Vascular Effects of Stroma and Stroma–Free Hemoglobin/Surgery, Gynecology & Obstetrics/(1979), 149, 874–876.

Gould, S.T. et al/The Development of Polymerized Pyridoxylated Hemoglobin Solution as a Red Cell Substitute/Ann. Emerg. Medicine/(1986), 15, 1416–1419.

Fermi G. et al/The Crystal Structure of Human Deoxyhaemoglobin at 1.74 a Resoltuion J. Mol. Biol./(1984), 175, 159–174.

Murray, N.E. et al/Molecular Cloning of the DNA Ligase Gene from Bacteriophage T4 II. Amplification and Preparation of the Gene Product/J. Mol. Biol./(1979), 132, 493–505.

Konotey–Ahulu, F.I.D. et al/Haemoglobin Korle–Bu (β73 Aspartic Acid →Asparagine) Showing One of the two Amino Acid Substitutions of Haemoglobin C Harlem/J. Med. Genet./(1968), 5, 107–111.

Devenuto, F. et al./Appraisal of Hemoglobin Solution as a Blood Substitute/Surgery, Gyneclogy & Obstetrics (1979), 149, 417–436.

Pigiet, V./The Role of Thioredoxin in Refolding Disulfide Proteins/Am. Biotechnology Laboratory/(1988), 6, 48–52.

Ladner, R.C. et al/The Structure of Horse Methaemoglobin at 2.0 a Resolution/J. Mol. Biol./(1977), 114, 385–414.

Kane et al, "Nine Days Post Thawing Red Cell Conservation in a Synthetic Medium" *Transfusion* 26(5):437–440 (Sep.–Oct. 1986).

Follette et al "Reducing Post Ischemic Damage by Temporary Modification of . . . Osmolarity", *J. Thorac. Cardiovasc. Surg.* 82:221–238 (Aug. 1981).

Boldt et al "Acute Preoperative Hemodilution . . . " J. Cardiothor. Vasc. Anes. 5(1):23–28 (Feb. 1991).

FIG. 1A

SEQUENCE: ALPHA

```
  1  GTG CTG TCT CCT GCC GAC AAG ACC AAC GTC AAG GCC GCC TGG   42
     Val Leu Ser Pro Ala Asp Lys Thr Asn Val Lys Ala Ala Trp

43  GGC AAG GTT GGC GCG CAC GCT GGC GAG TAT GGT GCG GAG GCC   84
     Gly Lys Val Gly Ala His Ala Gly Glu Tyr Gly Ala Glu Ala

85  CTG GAG AGG ATG TTC CTG TCC TTC CCC ACC ACC AAG ACC TAC  126
     Leu Glu Arg MET Phe Leu Ser Phe Pro Thr Thr Lys Thr Tyr

127  TTC CCG CAC TTC GAC CTG AGC CAC GGC TCT GCC CAG GTT AAG  168
     Phe Pro His Phe Asp Leu Ser His Gly Ser Ala Gln Val Lys

169  GGC CAC GGC AAG AAG GTG CTG GCC GAC GCG CTG ACC AAC GCC GTG  210
     Gly His Gly Lys Lys Val Ala Asp Ala Leu Thr Asn Ala Val

211  GCG CAC GTG GAC GAC ATG CCC AAC GCG CTG TCC GCC CTG AGC  252
     Ala His Val Asp Asp MET Pro Asn Ala Leu Ser Ala Leu Ser

253  GAC CTG CAC GCG CAC AAG CTT CGG GTG GAC CCG GTC AAC TTC  294
     Asp Leu His Ala His Lys Leu Arg Val Asp Pro Val Asn Phe

295  AAG CTC CTA AGC CAC TGC CTG CTG GTG ACC CTG GCC GCC CAC  336
     Lys Leu Leu Ser His Cys Leu Leu Val Thr Leu Ala Ala His

337  CTC CCC GCC GAG TTC ACC CCT GCG GTG CAC GCC TCC CTG GAC  378
     Leu Pro Ala Glu Phe Thr Pro Ala Val His Ala Ser Leu Asp

379  AAG TTC CTG GCT TCT GTG AGC ACC GTG CTG ACC TCC AAA TAC  420
     Lys Phe Leu Ala Ser Val Ser Thr Val Leu Thr Ser Lys Tyr

421  CGT
     Arg
```

FIG. 1B

SEQUENCE: BETA

```
1    GTG CAC CTG ACT CCT GAG GAG AAG TCT GCC GTT ACT GCC CTG          42
     Val His Leu Thr Pro Glu Glu Lys Ser Ala Val Thr Ala Leu

43   TGG GGC AAG GTG AAC GTG GAT GAA GTT GGT GGT GAG GCC CTG          84
     Trp Gly Lys Val Asn Val Asp Glu Val Gly Gly Glu Ala Leu

85   GGC AGG CTG CTG GTC GTC TAC CCT TGG ACC AGG TTC TTT              126
     Gly Arg Leu Leu Val Val Tyr Pro Trp Thr Arg Phe Phe

127  GAG TCC TTT GGG GAT CTG TCC ACT CCT GAT GCT GTT ATG GGC          168
     Glu Ser Phe Gly Asp Leu Ser Thr Pro Asp Ala Val MET Gly

169  AAC CCT AAG GTG AAG GCT CAT GGC AAG AAA GTG CTC GGT GCC          210
     Asn Pro Lys Val Lys Ala His Gly Lys Lys Val Leu Gly Ala

211  TTT AGT GAT GGC CTG GCT CAC CTG GAC AAC CTC AAG GGC ACC          252
     Phe Ser Asp Gly Leu Ala His Leu Asp Asn Leu Lys Gly Thr

253  TTT GCC ACA CTG AGT GAG TTC CAC TGT GAC AAG CTG CAC GTG          294
     Phe Ala Thr Leu Ser Glu Phe His Cys Asp Lys Leu His Val

295  GAT CCT GAG AAC TTC AGG CTC CTG GGC AAC GTG CTG TGT              336
     Asp Pro Glu Asn Phe Arg Leu Leu Gly Asn Val Leu Cys

337  GTG CTG GCC CAT CAC TTT GGC AAA GAA TTC ACC CCA CCA GTG          378
     Val Leu Ala His His Phe Gly Lys Glu Phe Thr Pro Pro Val

379  CAG GCT GCC TAT CAG AAA GTG GCT GTG GCT AAT GCC                  420
     Gln Ala Ala Tyr Gln Lys Val Ala Val Ala Asn Ala

421  CTG GCC CAC AAG TAT CAC
     Leu Ala His Lys Tyr His
```

BLOOD SUBSTITUTES

This application is a continuation of Ser. No. 08/062,780 filed May 17, 1993, now abandoned, which is a continuation of 07/443,950 filed Dec. 1, 1989, now abandoned, which is a continuation-in-part of Ser. No. 07/194,338 filed May 16, 1988, now U.S. Pat. No. 5,028,588, and incorporated by reference herein. Priority is claimed Under 35 U.S.C. 119 from U.K. Appl. 8711614, filed May 16, 1987, and incorporated by reference herein.

BACKGROUND OF THE INVENTION

1. Field of Invention

This invention relates to novel hemoglobin compositions useful as substitutes for red blood cells, and to methods of preparing same. It further relates to the preparation, using recombinant DNA technology, of mutant hemoglobins for use in such compositions.

2. Information Disclosure Statement

It is not always practical to transfuse a patient with donated blood. In these situations, use of a red blood cell substitute is necessary. The product must effectively transport $O_2$, just as do red blood cells. ("Plasma expanders", such as dextran and albumin, do not transport oxygen.) The two types of substitutes that have been studied most extensively are hemoglobin solutions and fluorocarbon emulsions.

Hemoglobin (Hgb) is the oxygen-carrying component of blood. Hemoglobin circulates through the bloodstream inside small enucleate cells called erythrocytes (red blood cells). Hemoglobin is a protein constructed from four associated polypeptide chains, and bearing prosthetic groups known as hemes. The erythrocyte helps maintain hemoglobin in its reduced, functional form. The heme iron atom is liable to oxidation, but may be reduced again by one of two enzyme systems within the erythrocyte, the cytochrome $b_5$ and glutathione reduction systems.

Hemoglobin exhibits cooperative binding of oxygen by the four subunits of the hemoglobin molecule (two alpha-globins and two beta-globins in the case of Hgb A), and this cooperativity greatly facilitates efficient oxygen transport. Cooperativity, achieved by the so-called heme-heme interaction, allows hemoglobin to vary its affinity for oxygen. Hemoglobin reversibly binds up to four moles of oxygen per mole of Hgb. At high oxygen concentration, such as that found in the lungs, the oxygen affinity is high and hemoglobin is almost saturated with oxygen. At low oxygen concentration, such as that found in actively respiring tissue, the oxygen affinity is lowered and oxygen is unloaded.

Oxygen-carrying compounds are frequently compared by means of a device known as an oxygen dissociation curve. This curve is obtained when, for a given oxygen carrier, oxygen saturation is graphed against the partial pressure of oxygen. The percentage of saturation increases with partial pressure according to a sigmoid relationship. The $P_{50}$ is the partial pressure at which the oxygen-carrying solution is half saturated with oxygen. It is thus a measure of oxygen-binding affinity; the higher the $P_{50}$, the more loosely the oxygen is held.

When the oxygen dissociation curve of a oxygen-carrying solution is such that the $P_{50}$ is less than that for whole blood, it is said to be "left-shifted."

The oxygen affinity of hemoglobin is lowered by the presence of 2,3-diphosphoglycerate (2,3-DPG), chloride ions and hydrogen ions. Respiring tissue releases carbon dioxide into the blood and lowers its pH (i.e. increases the hydrogen ion concentration), thereby causing oxygen to dissociate from hemoglobin and allowing it to diffuse into individual cells.

The ability of hemoglobin to alter its oxygen affinity, increasing the efficiency of oxygen transport around the body, is dependent on the presence of the metabolite 2,3-DPG. Inside the erythrocyte 2,3-DPG is present at a concentration nearly as great as that of hemoglobin itself. In the absence of 2,3-DPG "conventional" hemoglobin binds oxygen very tightly and would release little oxygen to respiring tissue.

Aging erythrocytes release small amounts of free hemoglobin into the blood plasma where it is rapidly bound by the scavenging protein haptoglobin. The hemoglobin-haptoglobin complex is removed from the blood and degraded by the spleen and liver.

It is clear from the above considerations that free native hemoglobin A, injected directly into the bloodstream, would not support efficient oxygen transport about the body. The essential allosteric regulator 2,3-DPG is not present in sufficient concentration in the plasma to allow hemoglobin to release much oxygen at venous oxygen tension, and free hemoglobin would be rapidly inactivated as an oxygen carrier by auto-oxidation of the heme iron.

Nonetheless, solutions of conventional hemoglobin have been used as RBC substitutes. The classic method of preparing hemoglobin solutions employs outdated blood. The red cells are lysed and cellular debris is removed, leaving what is hopefully "stromal-free hemoglobin" (SFH).

Several basic problems have been observed with this approach. The solution must be freed of any toxic components of the red cell membrane without resorting to cumbersome and tedious procedures which would discourage large-scale production. DeVenuto, "Appraisal of Hemoglobin Solution as a Blood Substitute", Surgery, Gynecology and Obstetrics, 149:417–436 (1979).

Second, as expected, such solutions are "left-shifted" (lower $P_{50}$) as compared to whole blood. Gould, et al., "The Development of Polymerized Pyridoxylated Hemoglobin Solution as a Red Cell Substitute", Ann. Emerg. Med. 15:1416–1419 (December 1986).

Third, SFH has a half-life in the circulatory system of only about 2–4 hours. This is because oxyHgb partially dissociates into a dimer that is small enough to be filtered by the kidney.

Finally, SFH has a high colloid osmotic pressure (COD). Thus, administration of SFH in a dose that would have the same oxygen-carrying capacity as a unit of packed red blood cells is inadvisable, since the high oncotic pressure (60 mm Hg) would cause a massive influx of water from the cells into the bloodstream, thus dehydrating the patient's tissues. This consideration limits the dose of SFH to about 6–8 gm Hgb/dl.

In an effort to restore the desired $P_{50}$, researchers added 2,3-DPG to the hemoglobin solution. Unfortunately, 2,3-DPG was rapidly eliminated from the circulation. Scientists then turned to other organic phosphates, particularly pyridoxal phosphate. Like 2,3-DPG, these compounds stabilized the "T state" of the Hgb by forming a salt bridge between the N-termini of the two beta chains. The pyridoxylated hemoglobin had a $P_{50}$ of 20–22 torr, as compared to 10 torr for SFH and 28 torr for whole blood. While this is an improvement over SFH, the pyridoxylated Hgb remains "high affinity" relative to whole blood.

Hemoglobin has been chemically modified (by intramolecular or intermolecular crosslinking) to increase intravascular retention and reduce osmotic pressure. Unfortunately, this polymerization also causes a "left shift" of the molecule's oxygen dissociation curve. Thus, for polymerized-pyridoxylated Hgb, the $P_{50}$ is about 18 torr.

For chemical modifications of hemoglobin, See Iwashita, U.S. Pat. No. 4,412,989 and 4,301,144 (with polyalkylene glycol), Iwasaki, U.S. Pat. No. 4,670,417 (with polyalkylene oxide), (with a polysaccharide); Nicolau, U.S. Pat. No. 4,321,259 and U.S. Pat. No. 4,473,563 (with inositol phosphate); Wong, U.S. Pat. Nos. 4,710,488 and 4,650,786 (with inositol phosphate and a polysaccharide); Bonhard, U.S. Pat. No. 4,336,248 (with other proteins or gelatin derivatives); Walder, U.S. Pat. No. 4,598,064 and U.S. Pat. No. 4,600,531 (intramolecularly crosslinked hemoglobin) and Ajisaka, U.S. Pat. No. 4,377,512 (with inulin).

The human alpha- and beta-globin genes have both been cloned and sequenced. Liebhaber, et al., P.N.A.S. (U.S.A.) 77:7054–58 (1980)(alpha-globin genomic DNA); Marotta, et al., J. Biol. Chem., 252: 5040–53 (1977)(beta-globin cDNA).

Nagai and Thorgerson (Nature, 309:810–812, 1984) expressed in *E. coli* a hybrid protein consisting of the 31 amino-terminal residues of the lambda cII protein, an Ile—Glu—Gly—Arg (Sequence ID: 16) linker, and the complete human beta globin chain. They cleaved the hybrid at the single arginine with blood coagulation factor Xa, thus liberating the beta-globin chain.

Later, Nagai, et al., P.N.A.S. (U.S.A.), 82: 7252–55 (1985) took the rDNA-derived human beta globin, naturally derived human alpha globin, and a source of heme and succeeded in producing active human hemoglobin. Additionally, they produced two semi-artificial analogues of the naturally occurring mutant hemoglobins Hb Nympheas and Hb Daphne by site-directed mutagenesis of the cloned beta-globin gene, expression of the modified gene, and combination of the rDNA-derived beta chain with naturally occurring alpha chain and a source of heme. Like the naturally occurring mutants, these semiartificial analogues exhibited increased oxygen affinity as compared to "normal" hemoglobin. In subsequent studies, the structural basis for this change in oxygen binding was established. Luisi and Nagai, Nature, 320:555–56 (1986); and cp. Nagai, et al., Nature, 329:858–860 (October 1987) (similar production of mutant hemoglobins with replacements of Val(67beta)E11).

Surprisingly, the expression of the human alpha globin gene in heterologous cells is substantially improved when this gene is fused to a portion of the beta globin gene.

SUMMARY OF THE INVENTION

We have discovered that the disadvantages of hemoglobin solutions as blood substitutes are overcome if a mutant hemoglobin species is selected which, in a typical cell-free blood substitute solution, would impart to the solution a $P_{50}$ comparable to that of non-mutant hemoglobin in RSC-bound state. Naturally occurring hemoglobin mutants which, in the erythrocyte environment, would impart to the erythrocyte a $P_{50}$ higher than the normal value for whole blood (28 torr) are of particular interest, both in their own right and for what they teach about the structural foundations of oxygen affinity. It is expected that many such "right-shifted" species,. outside the erythrocyte environment (and thus the right-shifting influence of 2,3-DPG), will assume a $P_{50}$ comparable to or greater than that of the normal $P_{50}$ for whole blood.

For the purposes of this invention, the term "conventional hemoglobin A" refers to the species of Hgb A whose alpha and beta chains are of the amino acid sequence given in FIGS. 1a and 1b. This is the species which is most frequently found in human erythrocytes and which imparts to such erythrocytes a $P_{50}$ of about 28 torr. A "hemoglobin A mutant" is defined as any species of hemoglobin A whose alpha or beta chain is of an amino acid sequence different from that set forth in FIG. 1. A "low affinity" hemoglobin A mutant is one which has a $P_{50}$ at least about 10% greater than that of "conventional hemoglobin A" in the same environment. It is particularly desirable that its $P_{50}$ be at least that twice of conventional (wild type) hemoglobin A in the absence of 2,3-DPG. A "recombinant" hemoglobin is one composed of an alpha and beta globin at least one of which is obtained by expression of a globin gene carried by a recombinant DNA molecule, whether the hemoglobin is a conventional hemoglobin or a mutant species.

A large number of naturally occurring low affinity Hgb A mutants are known. (See Table I). The mutations may appear in either the alpha or the beta chains of the molecule (or both, of course). Thus, Hgb Hazebrouck is a beta mutant $(38(C4):thr \geqq pro)$ whose $P_{50}$ is 36 (in whole blood), declining to 27–29 torr in vitro.

Clearly, one cannot depend on nature to provide an adequate supply of these low affinity mutants. Consequently, the mutant polypeptide chain will usually be prepared artificially, either by direct polypeptide synthesis, or, more preferably, by in vivo expression of the corresponding mutant gene in a suitable host cell. This gene may be obtained directly from the genome of the mutant erythrocyte precursor (a mature erythrocyte does not contain DNA), as a complementary DNA (cDNA) transcribed from the messenger RNA of the mutant erythrocyte precursor, by direct polynucleotide synthesis, or, preferably, by in vitro mutagenesis of the gene encoding conventional hemoglobin.

If one of the chains is identical to that of "conventional" hemoglobin, it may be obtained either naturally or synthetically. In addition, to create a functional hemoglobin molecule, it is necessary to provide the prosthetic heme groups and to couple the alpha and beta chains.

It is also within the contemplation of this invention to prepare and use non-naturally occurring low affinity mutants by appropriate modification and expression of the alpha or beta globin gene and subsequent assembly of a recombinant hemoglobin. Methods for selecting candidate sequences and evaluating their suitability for use in a blood substitute product are described herein.

We also have discovered that human alpha-globin may be obtained from a bacterial host by (1) constructing a fused gene which comprises not only the alpha-globin gene but also at least a portion of the beta globin gene, separated by spacer DNA encoding a selective protease cleavage site; (2) expressing the fused gene in the form of a fusion protein; and (3) cleaving the fusion protein at the aforementioned cleavage site in order to liberate the human alpha-globin. The use of the beta header results in about three-fold greater expression of the alpha globin.

As a result of this discovery, it is possible to prepare entirely artificial human hemoglobin, that is, hemoglobin in which both the alpha and beta globin chains are formed in cells other than human erythrocytes. Such fully artificial hemoglobin is ideal for use in blood substitute solutions. Of course, semi-artificial hemoglobins (one chain obtained from non-erythrocyte source) may still be used.

When extracted natural hemoglobin is used as a blood substitute, one must be concerned with the toxicity of red blood cell membrane components which might contaminate the product. It is known that erythrocyte stroma can cause dyspnea, bronchospasm, hypotension, arrythmia, disseminated intravascular coagulation, activation of complement, and renal, myocardial and hepatic changes associated with ischemia and acute inflammation. See Feola, Surgery, Gynecology & Obstetrics, 166:211–222 (March 1988); MacDonald, et al., F.A.S.E.B. J., 2(6) Abstr. 8217 (1988); Stone, et al., Surgery, Gynecology and Obstetrics, 149:874–876 (1979); Rabiner, et al, J. Exp. Med., 126: 1127–42 (1967). While purified preparations of natural hemoglobin are known (so called "stroma-free hemoglobin"), Feola comments, "a truly pure hemoglobin solution has not been produced."

Another concern with natural hemoglobin is contamination-with infectious agents communicated by blood. Bove, Progr. Hematol., 14: 123–145 (1986) reported that hepatitis viruses, cytomegalovirus, Epstein-Bart virus, serum parvoviruses, syphilis, malaria, filariasis, trypanosomiasis, babesiosis, numerous pathogenic bacteria, and AIDS are all transmitted by blood transfusions. AIDS has even been transmitted by blood transfusions screened as negative for HIV antibody. Ward, et al., New Engl. J. Med., 318: 473–78 (1988).

The alpha-globin-like polypeptide of the present invention may be identical in sequence to natural normal human alpha-globin or to a naturally occurring hemoglobin mutant, or it may be an alpha-globin mutant which is not known in nature. It may be a tandem repeat of two alpha globin-like sequences, see Ser. No. 07/374,161, incorporated by reference. The beta-globin-like polypeptide is analogously defined.

Mutant hemoglobins, whether of reduced or enhanced oxygen affinity, may be of value for altering $O_2$ concentrations in cell cultures, or for extracting $O_2$ from fluids.

We have further discovered that cysteine substitution mutants of alpha and/or beta globin may be prepared, facilitating the preparation of a mutant hemoglobin-like protein characterized by at least one intersubunit disulfide bond. Such disulfide bonded forms are expected to have the advantage of increased vascular retention. Since they are crosslinked into the T state, it is expected that they will also be right-shifted, unlike the polymerized, pyrridoxylated hemoglobins known in the art. Additional mutations may be introduced to reduce the oxygen affinity further. Alternatively, if the crosslinking reduces the oxygen affinity too much, additional mutations may be made to correct the oxygen affinity.

The appended claims are hereby incorporated by reference into this specification as a statement of the preferred embodiments.

BRIEF DESCRIPTION OF THE DRAWINGS

FIG. 1A shows the amino acid sequence of the alpha chain of conventional human hemoglobin and the nucleotide sequence encoding this chain (SEQ. I.D. NO.: 1).

FIG. 1B shows the amino acid sequence of the beta chain of conventional human hemoglobin and the nucleotide sequence encoding this chain (SEQ. I.D. NO.: 2).

DETAILED DESCRIPTION OF THE INVENTION

Figure 2A:
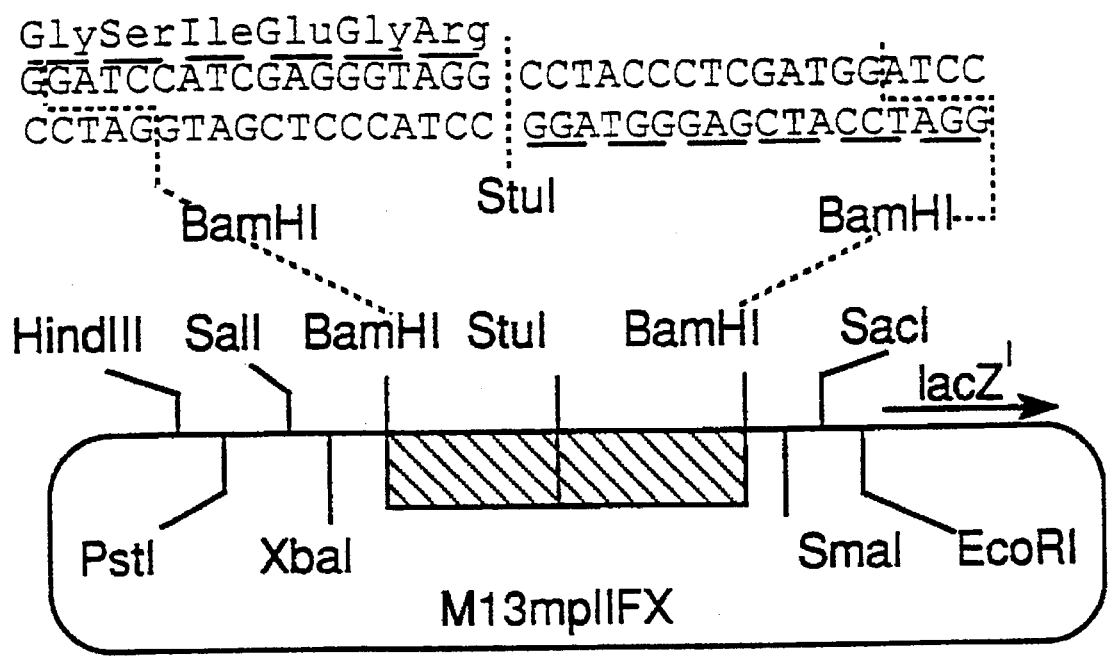
FIG. 2A shows selected DNA sequences and enzyme restriction maps of M13 mpl 1FX.

One aspect of this invention is the cloning and expression of an exogenous alpha globin gene in a suitable host. The host may be a procaryotic cell (such as a E. coli) or a eucaryotic cell (such as a yeast cell or a mammalian cell). The alpha globin gene will usually code on expression for a polypeptide corresponding to a naturally occurring human alpha globin, normal or abnormal, but may correspond to a nonhuman alpha globin, or indeed be a non-naturally occurring analogue of known alpha globins. Preferably, a mutant alpha globin is prepared and assembled into a low affinity hemoglobin mutant for use in a blood substitute composition.

The alpha globin gene is expressed as part of a fused gene which also codes on expression for at least a portion of the beta globin gene. In a preferred embodiment, the alpha and beta globin sequences are separated by spacer DNA encoding a selective protease cleavage site, in particular, a site susceptible to specific cleavage by Factor Xa.

Preferably, the aforementioned fused gene includes a subsequence which codes on expression for the 20 amino acid N-terminal of beta globin.

As previously noted, the alpha globin of the present invention is advantageously combined with rDNA-derived beta globin and a source of heme to obtain fully artificial (derived entirely from Sources other than blood) hemoglobin. Such hemoglobins, and especially low oxygen affinity hemoglobin mutants produced through use of selectively modified alpha and/or beta globin genes, are of value as blood substitutes. Semi-artificial hemoglobins, in which the only chain obtained from a non-erythrocyte source is a mutant sequence and the mutation imparts reduced oxygen affinity to the molecule, are also encompassed by the present invention and may also be used as blood substitutes. Unless otherwise indicated, the term "artificial" embraces both wholly and semi-artificial forms.

In order to appreciate possible strategies for designing low affinity alpha or beta mutants of hemoglobin for use as blood substitutes, it is necessary to understand the structure of the hemoglobin molecule.

The structure of conventional hemoglobin is well known. We herewith incorporate by reference the entire text of Bunn and Forget, eds., *Hemoglobin: Molecular, Genetic and Clinical Aspects* (W. B. Saunders Co., Philadelphia, Pa.: 1986) and of Fermi and Perutz "Hemoglobin and Myoglobin," in Phillips and Richards, *Atlas of Molecular Structures in Biology* (Clarendon Press: 1981).

The primary structure of a polypeptide is defined by its amino acid sequence and by identification of any modifications of the side chains of the individual amino acids.

About 92% of the normal adult human hemolysate is Hgb A (designated alpha2 beta2, because it comprises two alpha and two beta chains). The alpha chain consists of 141 amino acids (See FIG. 1a). The iron atom of the heme (ferroprotoporphyrin IX) group is bound covalently to the imidazole of his 87 (the "proximal histidine"). The beta chain is 146 residues long (see FIG. 1b) and heme is bound to it at His 92.

Other recognized hemoglobin species are Hgb $A_2$, Hgb $A_{1a}$, Hgb $A_{1b}$, and Hgb $A_{1c}$, as well as the rare species Hgb F, Hgb F$_1$, Hgb Gower-1, Hgb Gower-2, Hgb Portland, Hgb H, and Hgb Bart. They are distinguished from Hgb A by a different selection of polypeptide chains.

Segments of polypeptide chains may be stabilized by folding into one of two common conformations, the alpha helix and the beta pleated sheet. In its native state, about 75% of the hemoglobin molecule is alpha-helical. Alpha-helical segments are separated by segments wherein the chain is less constrained. It is conventional to identify the alpha-helical segments of the each chain by letters, e.g., the proximal histidine of the alpha chain is F8 (residue 8 of helix F). The non-helical segments are identified by letter pairs, indicating which helical segments they connect. Thus, non-helical segment BC lies between helix B and helix C. In comparing two variants of a particular hemoglobin chain, it may be enlightening to attempt to align the helical segments when seeking to find structural homologies. For the amino acid sequence and helical residue notation for conventional human hemoglobin A$_o$ alpha and beta chains, see Table 4.

The tertiary structure of the hemoglobin molecule refers to the steric relationships of amino acid residues that are far apart in the linear sequence, while quaternary structure refers to the way in which the subunits (chains) are packed together. The tertiary and quaternary structure of the hemoglobin molecule have been discerned by X-ray diffraction analysis of hemoglobin crystals, which allows one to calculate the three-dimensional positions of the very atoms of the molecule.

In its unoxygenated ("deoxy", or "T" for "tense") form, the subunits of hemoglobin (alpha1, alpha2, beta1, and beta2) form a tetrahedron having a twofold axis of symmetry. The axis runs down a water-filled "central cavity". The subunits interact with one another by means of Van der Waals forces and hydrogen bonds (and, in the case of deoxyhemoglobin, by "salt bridges"). The alpha1beta1 and alpha2beta2 interfaces remain relatively fixed during oxygenation. In contrast, there is considerable flux at the alpha1beta2 (and alpha2beta1) interface. In its oxygenated ("oxy", or "R" for "relaxed" form), the intersubunit distances are increased.

The deoxy conformation is stabilized by numerous interactions, including, for example, the hydrogen bond between Tyr42alpha and Asp99beta. In the oxygenated form, this bond is broken and a new one formed between Asp94alpha and Asn102beta.

Various different approaches to modification of hemoglobin may be adopted. In each case, a candidate mutant is selected which, on the basis of the available evidence, is believed to be likely to have a lower affinity for oxygen than conventional hemoglobin.

In making this selection, it is possible to consider not only the known effects of various mutations of human hemoglobin, but also the oxygen binding capacity of known forms of animal hemoglobins, and of related compounds such as carboxyhemoglobin, methemoglobin, myoglobin, etc.

Alpha Chain Mutants

Thanks to our success in overcoming the problems of expressing the alpha globin gene in a heterologous system, it is now possible to conveniently prepare alpha globin mutants.

Several low oxygen affinity hemoglobin alpha chain mutants are already known. Of these, Hb Titusville (alpha94Asp=>Asn), HbSetif (alpha94Asp≧Tyr), Hb Torino (alpha43Phe≧Val),Hb Hirosaki (alpha43Phe≧Leu) and Hb Moabit (alpha86Leu≧Arg) are of special interest.

Alpha globins are more readily oxidized than beta globins because the His(F8) to O$_2$ bond on the alpha chain is slightly stronger than on beta, so that an electron is more readily lost by the oxygen. Alpha globins could be modified to make them less oxidizable, for example, by the change alpha63His≧Gln or Val.

Chloride ion binds to the alpha chain by bridging between the N-terminal NH$_3^+$ and the hydroxyl of alpha131Ser. The effect of chloride binding is to increase the P$_{50}$ slightly. It is believed that by changing alpha131 to Glu, Asp or Asn one could achieve the same effect without resorting to chloride. Alternatively, the pK$_a$ of the N-terminal could be increased. The natural human N-terminal is valine, with a pK$_a$ of 9.72. This could be replaced with Ile (9.76), Pro (10.60) or Thr (10.43).

Beta globin mutants, and additional alpha globin mutants which are likely to impart reduced oxygen affinity, are discussed below.

Stabilizing the T state

It is not possible to raise the plasma concentration of 2,3-DPG sufficiently to maximize the oxygen carrying efficiency of free conventional hemoglobin in the blood. This problem can be overcome by stabilizing the T state with additional salt-bridges or hydrogen bonds introduced by protein engineering. The cross-linking of hemoglobin may itself stabilize the T structure to some extent.

Hydrogen bonds and ionic salt bridges are the predominant stabilizing forces on the surface of proteins. Hydrogen bonds are weak non-ionic bonds formed between electronegative atoms (e.g. oxygen, nitrogen, sulfur) and protons that are covalently attached to other electronegative atoms. Individually, hydrogen bonds are weak (e.g. −1 kcal/mol), but in a prote in there are hundreds to thousands of hydrogen bonds that collectively amount to a large stabilizing force. An example of an hydrogen bond that is important to hemoglobin structure is the hydrogen bond formed between alpha-asp$^{94}$ and beta-asn$^{102}$ in the oxy-state. When either of these residues is mutated to a residue that can no longer form this hydrogen bond the oxy state is destabilized and the molecule has a much lower O$_2$ affinity. Hg Kansas (beta thr$^{102}$), Hg Beth Israel (beta ser$^{102}$), Hg Richmond (beta lys$^{102}$), Hg St. Mande (beta tyr$^{102}$), Hg Titusville (alpha asn$^{94}$) and Hg Serif (alpha tyr$^{102}$) are all examples of the importance of this hydrogen bond. Other likely non-natural mutants that will achieve the same effect are beta asp$^{102}$, beta glu$^{102}$, beta arg$^{102}$, beta his$^{102}$, beta gly$^{102}$ and beta cys$^{102}$; alpha gln$^{94}$, alpha thr$^{94}$, alpha ser$^{94}$, alpha lys$^{94}$, alpha gly$^{94}$ and alpha arg$^{94}$.

Ionic interactions are salt forms formed between juxtaposed residues of opposite charge. These interactions are of much greater strength mole for mole than hydrogen bonds. An example of attraction of unlike charges would be the interaction between a lys and asp residue; at physiologic pH both of these residues are charged (positive and negative, respectively). Repulsion of two juxtaposed positive charges or two juxtaposed negative charges may also occur; interactions such as these are destabilizing.

Stabilization of the deoxy state of Hg by 2,3-DPG is an example of ionic interaction. The 2,3-DPG molecule is highly charged at neutral pH (5 negative charges) and interacts with eight residues in the 2,3-DPG pocket that are positively charged. It is felt that by engineering more positive charge into this binding pocket that 2,3-DPG would bind more tightly to the engineered Hgb than to HgbA. Another example is the alpha$_1$/beta$_2$ interface where alpha asp$^{94}$hydrogen bonds to beta asn$^{102}$. Replacing beta asn$^{102}$ with a negatively charged group such as asp or glu will interfere with oxystatestabilization by charge repulsion with the like charged alpha asp$^{94}$.

Thus, certain amino acid residue changes can facilitate the formation of the desired hydrogen bonds and salt bridges.

The T conformation can also be stabilized by the substitution of cysteine residues for other residues. Cysteine residues may be cross-linked by disulfide bonds. Examination of the published x-ray data of methemoglobin suggests that the alpha$_1$/beta$_1$ interface would be a logical place to put the disulfide. Conveniently, there are two alpha ala residues, G17 and G18 (ala is sterically similar to cys) adjacent to beta G14 cys. Hence, at first glance it is thought that alpha G17 or G18 would be likely spots for cys residues to be substituted. Further guidance about where to place disulfides may be provided by Thornton, J. M. J. Mol. Biol. 151, 261–287, 1981. Oxidation of cysteines to carry disulfide bonds (Cysteines) can be carried out by treatment with $O_2$ or catalyzed by thioredoxin (Pigiet, V Am. Biotech. Lab 6, 48–52, 1988).

It is not necessary that one of the cysteine residues used to form the disulfide bond be native to conventional hemoglobin. The following paired alpha and beta chain sites illustrate how both chains can be mentioned to promote disulfide bond formation:

i) Codon 41alpha Thr(ACC) -->Cys(TGC)
   Codon 99beta Asp(GAC) -->Cys(TGC)
ii) Codon 44alpha Pro(CCG) -->Cys(TGC)
    Codon 97beta His(CAC) -->Cys(TGC)
iii) Codon 94alpha Asp(GAT) -->Cys(TGC)
     Codon 101beta Glu(GAA) -->Cys(TGC)
iv) Codon 41alpha Thr(ACC) -->Cys(TGC)
    Codon 97beta His(CAC) -->Cys(TGC)
v) Codon 92alpha Arg(CGT) -->Cys(TGC)
   Codon 37beta Trp(CAC) -->Cys(TGC)
vi) Codon 92alpha Arg(CGT) -->Cys(TGC)
    Codon 40beta Arg(CGT) -->Cys(TGC)
vii) Codon 96alpha Val(GTT) -->Cys(TGC)
     Codon 101beta Glu(GAA) -->Cys(TGC)

Modifying Residues Near the Oxygen Binding Site

Heme (haem) is the prosthetic group of hemoglobin, myoglobin, catalase, peroxidase, and cytochrome b. The heme is inserted in a cleft between the E and F helices. The heme iron is linked covalently to the imidazole nitrogen of the "proximal" F8 histidine. The "distal" E11 valine appears to guard the access of oxygen to the heme pocket.

Val-E11 and His-E7 are highly conserved residues which are in Van der Waals contact with the oxygen molecule liganded to the heme iron atoms of hemoglobin; by replacing these residues the intrinsic oxygen affinity of hemoglobin can be altered. Val-E11 has been replaced with Ile, Leu, Ala and Met. The oxygen affinity of the Ala-E11beta mutant was higher than that of HbA; that of the Ile-E11beta mutant was lower. X-ray crystallographic study of the latter mutant showed that the delta-methyl group of the Ile side chain must be pushed to one side if oxygen is to bind to the iron atom.

Another alteration that we have made is beta His63≧Phe. This mutant has an extraordinarily low oxygen affinity (See Table 3).

It has therefore been shown that the oxygen affinity of hemoglobin can be altered at will by replacing residues close to the oxygen binding site. By adjusting oxygen affinity in this way the efficiency of oxygen transport can be maximized in the absence of allosteric effectors such as 2,3-DPG.

The following residues of human deoxyhemoglobin are, on a nearest atom-to-nearest atom basis, within 4 angstroms of the heme moiety: Alpha B13(D)Met, C7(E)Tyr, CEi(D) Phe, CE3(E)His, CE4(D)Phe, E7(D)His, E10(D)Lys, E11 (D)Val, E14(D)Ala, F4(P)Leu, F7(P)Leu, FS(P)His, FG3(P) Leu, FG5(P)Val, G4(P)Asn, G5(P)Phe, G8(D)Leu, H15(P) Val and H19(P)Leu; and Beta B13(D)Leu, C7(E)Phe, CDI (D)Phe, CD3(E)His, CD4(D)Phe, E7(D)His, E10(D)Lys, E11(D)Val, E14(D)Ala, F4(P)Leu, F7(P)Leu, F8(P)His, FG3(P)Leu, FGS(P)Val, G4(P)Asn, GS(P)Phe, GS(D)Leu, H15(P)Val, and H19(P)Leu. See Fermi, et al., J. Mol. Biol., 175: 159–174 (1984). (In the above list, "P" denotes "proximal" "D" "distal", and "E" "edge-on".)

These residues are therefore candidates for modification. Consideration should also be given to pairs contacted through bound water molecules. See Ladnet, et al., Mol. Biol., 114:385–414 (1977).

Mutations of beta residues 42 (CD1), 45 (CD4) and 70 (E14) are of particular interest. Other beta residues of interest include 43 (CE1), 46 (CE4), 58 (E7), 61 (E10) and 62 (E11). Alpha residues of interest include 43 (CE1), 46 (CE4), 58 (E7), 61 (E10) and 62 (E11).

In general, mutations around the heme-$O_2$ binding site that interfere with $O_2$ binding are also desirable because of their low-affinity $O_2$ binding nature. Replacing residues that are adjacent to the face of heme that binds $O_2$ can result in lower affinity. A naturally occurring mutant Hg Bristol (beta$^{67}$ val≧asp) has been described with low affinity. Other mutants that are desirable are the beta ile$^{67}$ described herein, beta asp$^{67}$ and beta glu$^{67}$. Other residues are also in the vicinity of the $O_2$ binding site. Histidine E7 (beta his$^{63}$) can be replaced with phe which results in very low $O_2$ affinity. The other likely residue for mutation is beta phe$^{42}$; replacement with trp is likely to result in low $O_2$ affinity. The corresponding residues of the alpha chain may be altered instead of, or in addition to, these preferred mutations of the beta chain.

Replacing Residues at the Alpha$_1$ Beta$_2$ Contact and the Central Cavity

The oxygen affinity and cooperativity of hemoglobin depend on the relative stabilities of the T (low affinity) and R (high affinity) quaternary states. These two states are in equilibrium with each other but one state may be favored by mutations at the alpha$_1$ beta$_2$ contact or in the central cavity. There are many naturally occurring mutations at these sites, and careful study of these should be of value in designing a hemoglobin molecule with the desired properties.

Thus alpha I residues 37 (C2) Pro, 38 (C3) Thr, 40(CS) Lys, 41(C6)Thr, 42(C7)Tyr, 44(CD2)Pro, SS(F9)Ala, 91(FG3)Leu, 92(FG4)Arg, 94(G1)Asp, 95(G2)Pro, 96(G3) Val, 97(G4)Asn, 140(HC2)Tyr, and 141(HC3)Arg are all known to lie within 4 angstroms of at least one residue of the beta2 chain of human deoxyhemoglobin. Similarly, beta2 residues 146 (HC3) His, 145 (HC2) Tyr, 105 (G7) Leu, 102(G4)Asn, 101(G3)Glu, 100(G2)Pro, 99(G1)Asp, 98 (FGS)Val, 97 (FG4)His, 43 (CD2)Glu, 41(C7)Phe, 40(C6) Arg, 37(C3)Trp, 36(C2)Pro, 35(C1)Tyr, and 34(B16)Val lie on the other side of the alpha1beta2 interface of human deoxyhemoglobin.

Mutation of beta102(G4)Asn is particularly preferred. Hg Kansas is a known low affinity mutant in which this residue is altered to Thr. As previously mentioned, the oxy state is stabilized by a hydrogen bond between beta Asn102 and alpha Asp94. The preferred mutation would disrupt this hydrogen bond.

Another favored mutation at this site is to beta Asp102. The negative charge-negative charge repulsion between this group and the alpha Asp94 would further destabilize the oxy state.

Still other preferred mutations at the beta102 locus would be to Ser (Hb Beth Israel), Lys (Hb Richmond) and Tyr (Hb St. Mande).

Increasing the Stability of Hemoglobin

Inside the erythrocyte the cytochrome $b_5$ and glutathione reduction systems serve to maintain hemoglobin in the active ferrous form. Free hemoglobin in the bloodstream would rapidly be at least partially oxidized to the ferric state since there is no such means of keeping it in the reduced form outside the red cell. It is possible to stabilize the ferrous form by replacing the Val-E11 residue with a large aliphatic amino acid such as Ile or Leu. A large side chain at this position prevents electron donors from reaching the iron atom and so slows the rate of autoxidation. The $His63 \geqq Phe$ mutant is also of interest.

If hemoglobin is cross-linked both intermolecularly to form higher molecular weight aggregates and intramolecularly to prevent dissociation into dimmers then it will neither react with haptoglobin nor pass through the glomerular membrane of the kidney. If the oxygen binding properties of haemoglobin are to be unaffected it is important that the cross-linking does not prevent conformational change of the protein. This is because the hems-hems interaction arises from a reversible transition between two quaternary structures: the T structure with low oxygen affinity. These two structures with high oxygen affinity. These two structures differ in the contact between the $alpha_1$ and $beta_2$ subunits. Therefore this contact should be allowed to undergo the conformational changes accompanying oxygen association and dissociation.

Site-directed mutagenesis can be used to replace certain surface residues of haemoglobin with cysteinyl residues. Protein engineering techniques similar to those used to introduce new disulfide bridges to lysozyme, subtilisin and dihydrofolate reductase can be used. Hemoglobin molecules carrying such —SH groups can be cross-linked by disulfide bridges or via a bifunctional thiol reagent. It should also be noted that there is a natural mutant (Hb Ranier) in which His 143 beta is replaced by Cys and the newly introduced cysteine forms a disulfide bridge with Cys 93 beta in vivo. This mutant is more stable than native Hb.

Table 2 is a list of candidate, non-naturally occurring hemoglobins which are expected to exhibit a lower affinity for oxygen than does conventional hemoglobin.

After determining the amino acid sequence changes which distinguish the desired hemoglobin from conventional hemoglobin, it is necessary to design the expression vector. The most convenient starting point is a nucleotide sequence which codes upon expression for conventional hemoglobin. This sequence then may be modified by site-specific mutagenesis.

Techniques of site-specific mutagenesis are well known, and this invention is not limited to any particular technique. The two principal techniques are the gapped duplex A. A., Kruse, K. B., Brown, J. L. BioTechniques 6, 338–339, 1988) and M-13 (Zoller, M. J. and Smith, M. Meth. Enz. 100, 468–500, 1987) methods.

Alternatively, a subsequence with the desired mutation may be synthesized and then ligated to other subsequences to form the desired molecule.

The gene must be placed under the control of a promoter. Either a constitutive or an inducible promoter may be used; the advantages and disadvantages of each are wellknown in the molecular biology art. A promoter must be chosen which is functional in the host. Thus, a bacterial promoter would be chosen if the expression vector is to be introduced into a bacterial host, a yeast promoter, if a yeast host, and a mammalian promoter, if a mammalian cell host. It should be understood that the promoter of a viral gens of a virus which infects the chosen host cell may also be used. The present invention does not depend upon the choice of either the promoter or the host. However, it is desirable to choose a host so that the subsequent purification of the mutant hemoglobin is not unduly complicated.

For the same reason, it is preferable, but not required, that the mutant hemoglobin be expressed as a moiety of a fusion protein. Attempts to express the alpha chain other than as a fusion protein were largely unsuccessful. However, the entire alpha chain sequence could be expressed as part of a fusionprotein including a portion of the beta chain, and separated from the latter by a spacer providing a selective cleavage site. The hemoglobin is obtained merely by placing the secreted fusion protein in an appropriate cleavage environment. Numerous fusion protein/cleavage system combinations are now known in the art.

After expressing, recovering and purifying the mutant hemoglobin, its $P_{50}$ is measured in accordance with the protocol set forth in the Reference Example. Preferably, its $P_{50}$ is at least 10% higher than that of conventional hemoglobin A when measured in the same environment.

While it is not practical to combine stroma-free conventional hemoglobin with sufficient 2,3-DPG to restore its $P_{50}$ to intra-erythrocyte levels, it may be possible to combine a modestly right-shifted mutant hemoglobin with a small amount of 2,3-DPG or functionally similar organic phosphate (e.g., pyridoxal phosphate or ATP-dialdehyde) so as to mimic the oxygen-carrying capacity of whole blood. The half life of the organic phosphate may be improved by encapsulating the organic phosphate and the mutant hemoglobin in a liposome to obtain a "simulated erythrocyte," or by covalently attaching the organic phosphate group to the hemoglobin.

Reference Example

Our preferred method of measuring the $P_{50}$ of purified hemogoblin solutions for the purpose of the appended claims is as follows.

Hemoglobin-oxygen equilibrium data are measured using a thin film technique (Imai, K. Meth. Enz. 76, 438–449, 1981). A sample of hemoglobin (0.6 mM) in buffer (50 mM Bis-Tris or 100 mM HEPES), pH 7.4, 0.1M NaCl, is applied to the cell and then equilibrated at 25° C. The hemoglobin is saturated with $O_2$ by a stream of air, or air/$O_2$ if the hemoglobin has low $O_2$ affinity or if the local barometric pressure prevents abient oxygen from achieving a high enough partial pressure to saturate the molecule. Deoxygenation is achieved by closing the cell to $O_2$ flow and flushing the cell with $N_2$ (>99.98% pure). The oxygen equilibrium curve is obtained by plotting the change in absorbance at 560 nm against the pressure of $O_2$ in the cell. Percent saturation is determined by measuring the $A^{560}$ at a given partial pressure (i) divided by the $A^{560}$ of the beginning, totally saturated Hgb solution Hgb solution [$A^{560}$ (i)/$A^{560}$ (100%) ×100=% saturation]. The $P_{50}$ is defined as the partial pressure (i) of $O_2$ required to cause 50% saturation of $O_2$ binding sites.

$P_{50}$ may also be measured under other conditions, but it should be noted that many environmental factors affect hemoglobin's oxygen affinity. The effect of Ph, $CO_2$, inorganic anions, organic phosphates and temperature on $P_{50}$ are discussed in Bunn and Forget, HEMOGLOBIN:MOLECULAR, GENETIC AND CLINICAL ASPECTS 37–47, 95–98 (W. B. Saunders Co.: 1986).

Since many determinations of whole blood oxygen binding curves are made under standard physiologic conditions (37° C. pH=7.4 $PCO_2$=40 mm Hg), it may be necessary to adjust literature figures. In this context, it should be noted that a 10° C. increase results in nearly a two-fold increase in $P_{50}$, while the dependence of $P_{50}$, while the dependence of $P_{50}$ on pH is approximately given as delta log Psi delta pH=–0.5.

Comparing $P_{50}$ values of purified Hb preparation to $P_{50}$ values of whole blood can be problematic. Whole blood, or isolated RBC's, contain many components that naturally modulate the shape of the-hemoglobin-oxygen binding curve. The RBC encapsulates Hgb in the presence of a high concentration of the effector molecule 2,3-DPG; a molecule that causes Hgb to have a markedly lower affinity for $O_2$. Other intra-erythrocyte components also affect the shape of the binding curve: ATP, $Cl^-$, $CO_2$, $H^+$, orthophosphate, methemoglobin and carboxyhemoglobin. These substances are not normally present in purified HgB solutions and thus, the $P_{50}$ value of purified Hgb is lower than that found in whole blood. One very important modulator of Hgb-oxygen affinity is $Cl^-$ ion. $Cl^-$ ion is found outside the erythrocyte in the blood serum at a physiologic concentration of approximately 0.15M. Since $Cl^-$ causes a lower $O_2$ affinity, a Hgb solution with a $P_{50}$ measured in vitro may well have much lower $O_2$ affinity if infused into the blood stream. Another problem with measuring $O_2$ binding of whole blood is that RBCs are quite fragile and in the process of manipulating the erythrocyte into the instrument used to measure the $O_2$ binding it is inevitable that at least a small percentage of the RBCs will lyse. Lysed RBCs leak Hgb into the surrounding media away from 2,3-DPG; hence, since free Hgb has a higher affinity than intraerythrocyte Hgb, lysed RBCs will have a higher $O_2$ affinity and can cause a falsely low $P_{50}$ value for whole blood $P_{50}$ determinations. It is widely accepted that under physiologic conditions whole blood has a $P_{50}$ value of 26–28 mmHg. When Hgb is isolated from whole blood, however, the measured $P_{50}$ is on the order of 1–10 mmHg depending on the investigators experimental conditions. For these reasons it is most accurate to measure Hgb-oxygen equilibria with purified Hgb molecules under strict conditions of buffer, pH and salt concentration. Unfortunately, there are no accepted "standards" for all. investigators to measure Hgb oxygen binding in in vitro systems.

Still, as many mutant hemoglobins are first identified in patient's whole blood, one would like to be able to compare the relative affinities of native and mutant Hgb for $O_2$, between whole blood and purified Hgb preparations. An example of this is Hgb Chico (beta $lys^{66} \geq thr$) (Table 1). If one examined only the $P_{50}$ value of the purified mutant Hgb (10.1 mmHg)one would note that Hgb has a $P_{50}$ value less than that for normal whole blood (27.2 mmHg). Still, when that hemoglobin is measured in RBCs under physiologic conditions it is apparent that it does have a higher $P_{50}$ than normal whole blood (38 mmHg). One cannot predict the degree that the $P_{50}$ value will change going from whole blood Chico to a purified Hgb Chico if it were infused into the bloodstream as a blood substitute. One can conclude, however, that the $P_{50}$ will be higher than it is in pure form, and that by reacting the mutant Hgb with organic phosphates that $R_{50}$ will be even higher.

Note also that whole blood oxygen binding curves are customarily determined under standard physiologic conditions 37° C. pH 7.4, $PCO_2$=40 mmHg) and red cell 2,3-PDG varies with age, sex and condition.

EXAMPLE 1

Production of Artificial Conventional Hemoglobins

Construction of M13 mp11 FX

M13 mp11 FX encodes a sequence (Ile—Clu—Cly—Arg (SEQUENCE ID:16)) including the recognition site for factor $X_a$. This M13 derivative can be used to join any coding sequence to the factor $X_a$ recognition sequence. See Nagai, EP Appl 161,937 (CELLTECH LTD.) However, this invention is not limited to the use of either M13 or of the factor Xa cleavage system.

All DNA manipulations were carried out essentially as described by Maniatis et al ('Molecular Cloning' Cold Spring Harbour, New York, 1982). A temperature-sensitive lysogenic strain MZ-1 (gal$K_{am}$ 8attL $BamN_7N_{53}$cI857 H1, his-, ilv-, bio-, $N^+$, a gift from Dr. K. McKenney and available on request from Medical Research Council) was used as a host strain for plasmids containing lambda $P_L$ promoter and transformation was carried out by the method of Remaut et al (Gene 15, 81–93 (1981)). Other promoters and host strains could have been employed.

T4 DNA ligase was prepared from strain NM989 (Murray et al, J Molec Biol 132, 493–505 (1979) and Tait et al, J Biol. Chem 255, 813–815 (1980)). Restriction enzymes were purchased from New England BioLabs.

Two oligonucleotides dTACCCTCGATGGATC [SEQ ID:13] and dCATCGAGGGTAGGCC [SEQ ID:14] were synthesized by a phosphotriester method on a controlled pore glass support (Sproat et al, Tetrahedron Lett, 24, 5771–5774 (1983)) and purified by HPLC (Gait et al, Nucleic Acids Research 10, 6243–6254 (1982)) These oligonucleotides encode the peptide sequence (gly)—ser—ile—glu—gly—arg [SEQ ID:15] in a BamH1-stu1 linker. The two oligonucleotides were allowed to anneal after phosphorylation with T4 polynucleotide kinase (P-L, Biochemicals) and r[gamma-$^{32}$P]ATP (3000 Ci/m mol, Amersham) and ligated to form concatamers. The DNA was then digested with Bam HI and cloned into the dephosphorylated Bam HI site of M13 mp11 (Vieira et al, Gene 19, 259–268 (1982)) to yield M13 mp11 FX, as shown in FIG. 1a, which forms blue plaques in the presence of isopropyl-beta-D-thiogalacto-pyranoside and 5-bromo-4-chloro-3-indolyl-beta-d-galactoside (Sigma).

Construction of mp11 FX alpha-globin 40 micro g of cloned human alpha-globin cDNA were digested with the restriction enzymes Nco I and Apa I. The single-stranded ends of the excised alpha-globin fragment were trimmed by incubation at 0° C. for 10 minutes with 200 units of mung bean nuclease (P-L Biochemicals) in 30 mM sodium acetate pH 4.6, 50 mM sodium chloride, 1 mM zinc chloride, 5% glycerol. The alpha-globin sequence was then cloned into the Stu I site of M13 mp11 FX described above (Nagai & Thogersen, Nature 309, 810–812). The DNA sequences of several clones were determined (Sanger et al Proc. Natl. Acad. Sci. USA, 74, 5463–5467 (1977)) and a clone in which the first valine codon of the alpha-globin gene was joined to the DNA sequence encoding the factor $X_a$ recognition site (Ile—Glu—Gly—Arg) was named mp11 FX alpha-globin.

Construction of pLcII beta and pLcIIFX beta

Plasmids pLcIIFX beta and pLcII beta direct efficient production of a hybrid protein consisting of the 31 amino-terminal residues of the lambda cII protein and the complete human beta-globin, with and without the factor $X_a$ cleavage site, respectively.

The Eco-Hind III fragment containing the multi-restriction sites was cut out from M13 mp10 (Vieira eta al, supra) and ligated to Eco RI-Hind III cut plc245 (Remaut et al, supra) to form pLmp10. The 319 bp Alu I fragment containing the nutR, $t_{R1}$ sites and a part of the cII gene was cut out from pKG1805 (McKenney, K PhD Dissertation, The Johns Hopkins University (1982)) and cloned into the Sma I site of M13 mp10 in the same, orientation with respect to the beta-galactosidase alpha-peptide gene. The Eco RI-Hind III fragment containing the lambda DNA sequence was then cut out and cloned into the Eco RI-Hind III site of pLmp10 to yield pLcII.

A complete human beta-globin cDNA sequence was reconstructed by joining restriction fragments prepared from an incomplete cDNA clone (pJW102) (Wilson et al, Nucleic Acids Research 5, 563–581 (1978)) and a genomic DNA clone (Lawson et al, Cell 21, 647–651 (1980)) and cloned into the Sma I-Hind III site in M13 mp9. M13 mp9 beta cDNA thus obtained was opened at the Nco I site which is located at the initiation codon and treated with Klenow DNA polymerase-(Boehringer Mannheim) in the presence of 100 micro M 4dNTP to obtain flush ends. The beta-globin cDNA sequence was then cut out with Hind III and inserted into the Bam HI (filled-in)-Hind III site of pLcII so that the beta-globin gene was fused to the lambda cII gene in phase via a small linker DNA derived from M13 mp10.

Figure 2B:
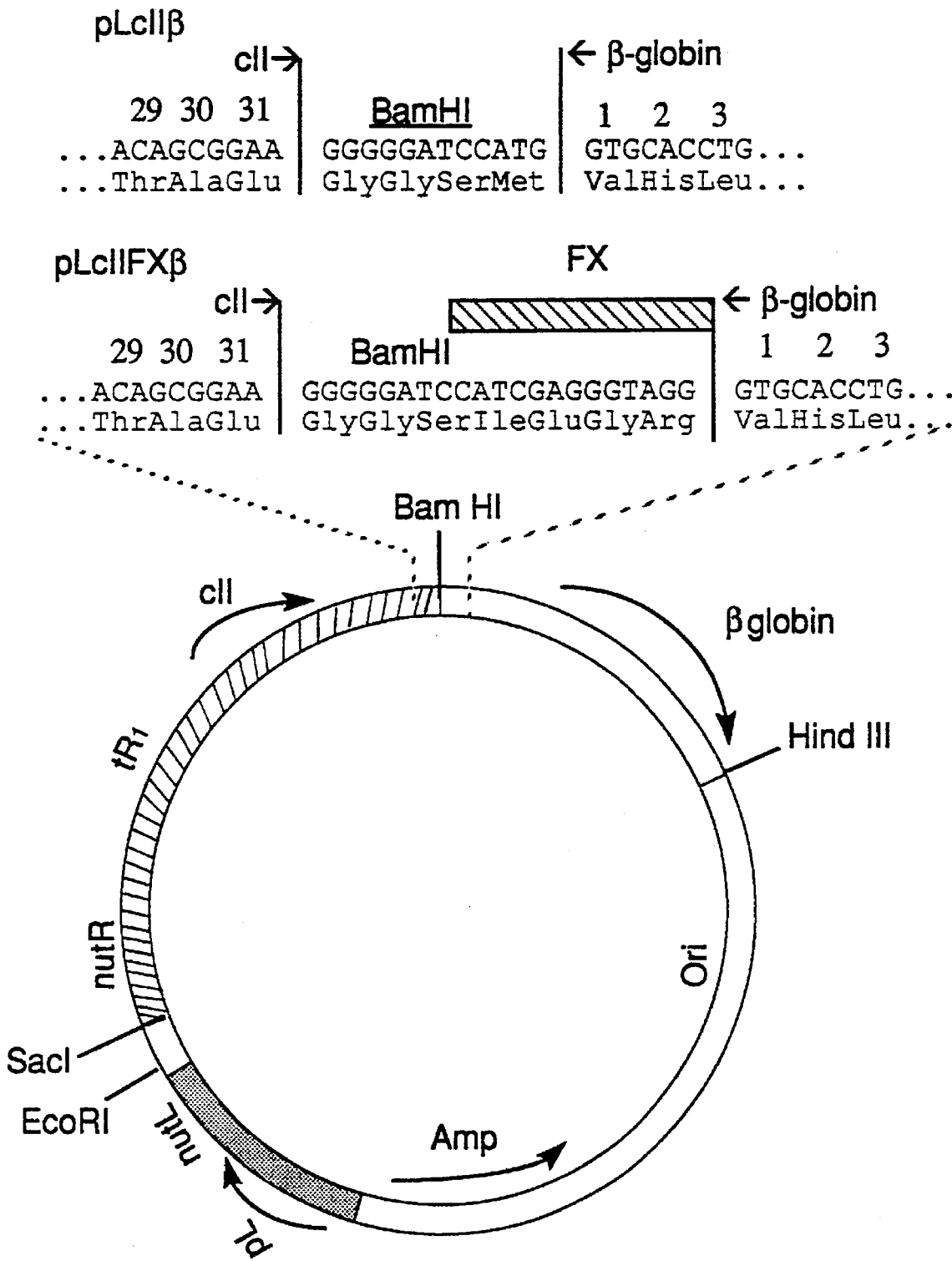
FIG. 2B shows the same for pLcIIFX beta and pLcII beta.
Figure 2C:
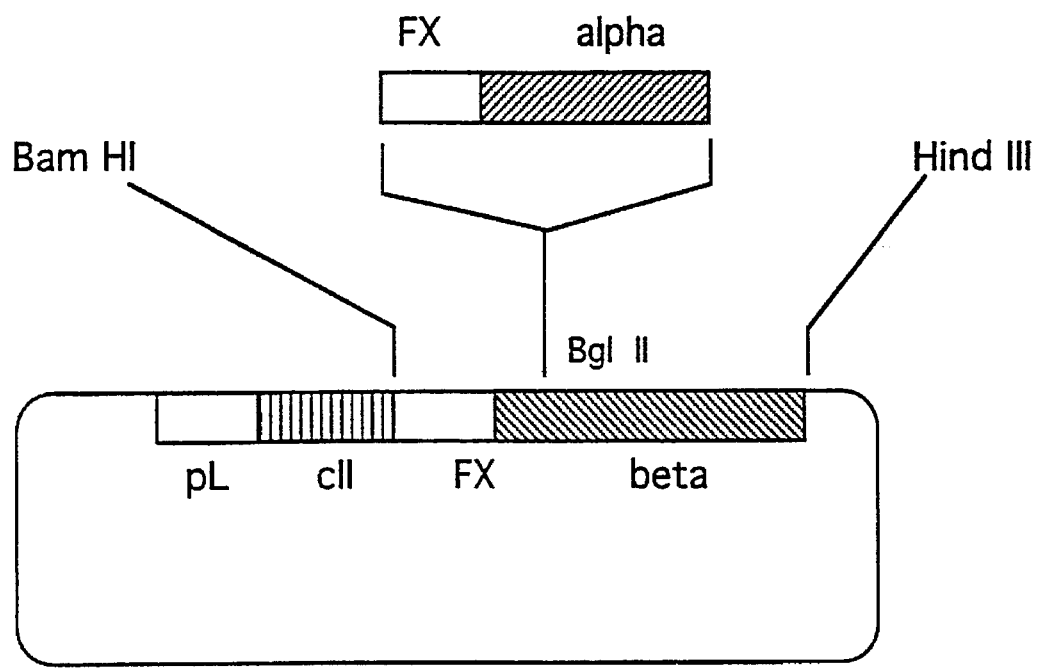
FIG. 2C shows selected DNA sequences and enzyme restriction maps of pLCIIFX-beta-FX-alpha.
Figure 2D:
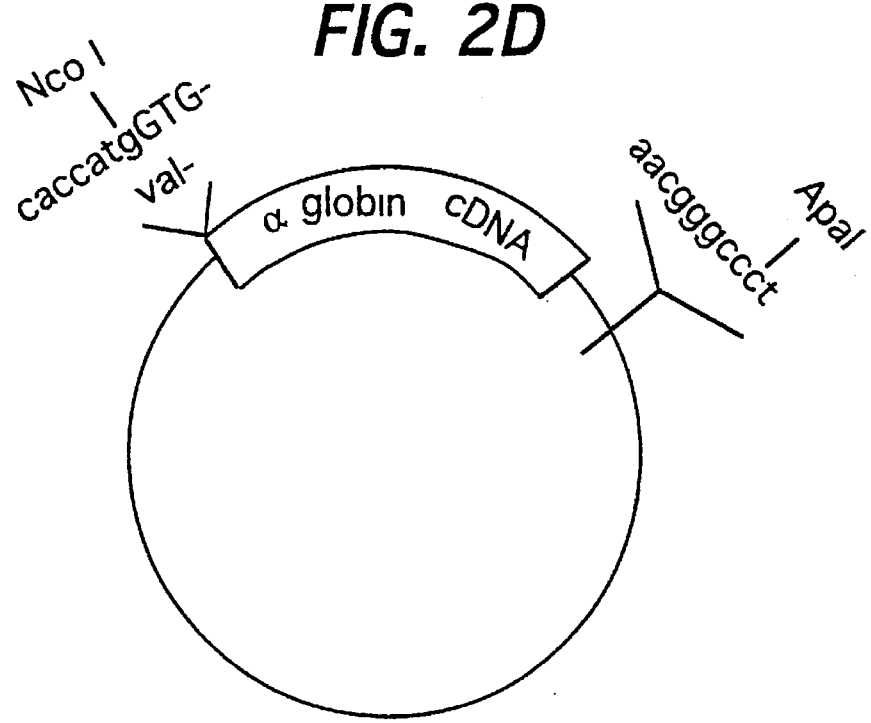
FIG. 2D shows pLCIIFX alpha. Note that pLCIIFX alpha lacks the codon encoding beta His 2 shown in FIG. 2b.
Figure 3:
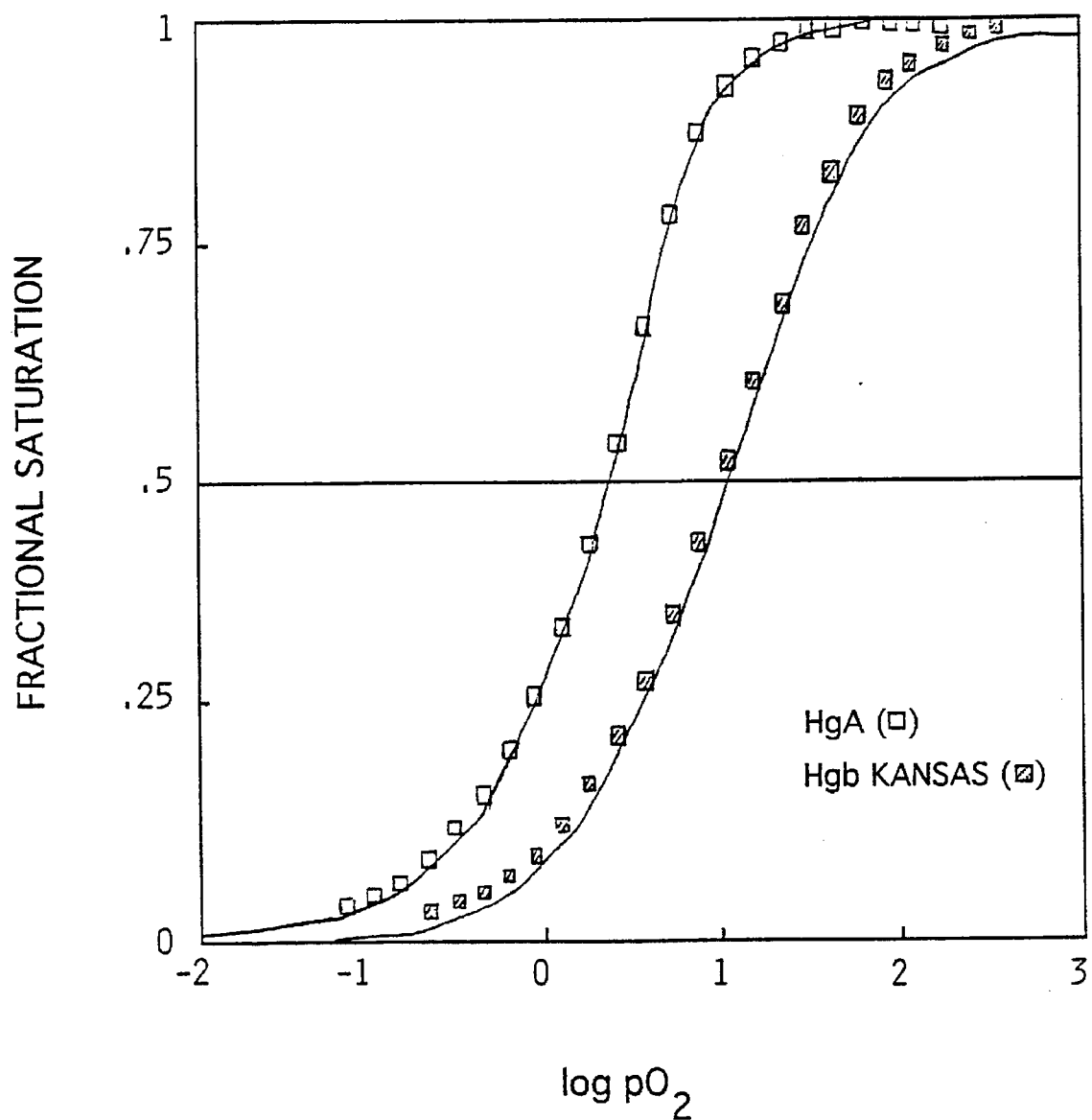
FIG. 3 shows equilibrium oxygen binding curves for artificial conventional human hemoglobin and mutant human hemoglobin having the structure of Hb Kansas.

In order to construct pLcIIFX beta, M13 mp9 beta cDNA was opened with Nco I and 40 micro g of DNA was treated with 200 units of mung bean nuclease (P-L Biochemicals) in 30 mM Na-acetate pH 4.6, 50 mM NaCl, 1 mM $ZnCl_2$, 5% glycerol at 0° C. for 10 min to remove the 5, protruding end. The beta-globin cDNA sequence was cut out with Hind III and cloned into the Stu I-Hind III cut M13 mpII FX. The DNA sequence was determined by the dideoxy chain termination method (Sanger et al, PNAS 74, 5463–5467 (1977)) to ensure that the first valine codon of the beta-globin gene was preceded by the DNA sequence coding for Ile—Glue—Gly—Arg [SEQ ID:16]. Then, the Bam HI fragment containing a part of the beta-globin sequence was cut and cloned into Barn HI digestted pLcII beta to form pLcIIFX beta, as shown in FIG. 2b.

Construction of pLcII FX beta FX alpha

M13 mp11 FX beta-globin DNA was prepared in single-stranded form and a BglII site was introduced into the beta-globin sequence using a mutagenic oligodeoxynucleotide, dACCAACTTCAGATCTGTTAC-CTTG [SEQ ID:17]; called KN83, to obtain mpII cII FX beta FX. The replicative form of this mutant clone was digested with SacI and Hind III, and the resulting cII FX beta FX fragment was cloned into Sac I/Hind III cut pLmpII to form pLcII FX beta FX. This recombinant plasmid was digested with BglII and the 5' terminal phosphate groups of the linear DNA were removed with calf intestinal alkaline phosphatase. The replicative form of mpII FX alpha-globin was digested with BamH1 and the FX alpha-globin containing fragment was ligated with the linearised pLcII FX beta FX to form pLcII FX beta FX alpha. This plasmid encodes a fusion protein consisting of the 31 amino-terminal residues of the lambda phage cII protein, the tetrapeptide Ile—Glu—Gly—Arg (SEQUENCE ID:16), the 20 amino-terminal residues of human beta-globin, the tetrapeptide Ile—Glu—Gly—Arg (SEQUENCE ID:16) and human alpha-globin at the carboxyl end. Transcription of the fusion protein gens is initiated at the lambda $P_L$ promoter and is regulated by lambda repressor.

Expression of Recombinant Conventional Alpha and Beta Globin

A defective lambda phage lysogenic strain of *E. coli* QY13 (a gift from S. Brenner, and available on request from Medical Research Council) harboring pLcIIFX beta FX alpha-globin or pLcIIFX beta-globin was grown at 30° C. in 2xTY medium (16 g tryprone, 10 g yeast extract and 5 g sodium-chloride-litre) in the presence of ampicillin (25 micro g/ml). When the optical density (600 nm) reached 1.5–1.6, the temperature was quickly raised and maintained at 42° C. for 15 min, followed by further incubation at 37° C. for 3–4 hr. The cells were harvested and frozen in liquid nitrogen.

The cells (100 g) were thawed and suspended in 80 ml of 50 mM Tris-HCl (pH 8.0)/25% sucrose (wt/vol)/1 mM EDTA and lysed by addition of lysozyme (200 mg). Then, $MgCl_2$, $MnCl_2$ and DNase I were added to final concentration of 10 mM, 1 mM and 10 micro g/ml, respectively. After 30 min incubation 200 ml of 0.2M NaCl/1% deoxycholic acid/1.6 % Nonidet P-40 (vol/vol)/20 mM Tris-HCl(pH7.5) /2 mM EDTA were added to the lysate, which was then centrifuged at 5000xg for 10 min. Then the pellet was suspended in 0.5 % Triton X-100/1 mM EDTA and centrifuged. This procedure was repeated until a tight pellet was obtained. The protein pellet was finally dissolved in 8M urea/25 mM Tris-HOAc (pH5.0)/1 mM EDTA/1 mM dithiothreitol in the case of cIIFX beta-globin fusion protein. In the case of cIIFX beta-PX-alpha-globin fusionprotein, the pellet was first dissolved in 6M guanidine hydrochloride/25 mM Tris-HOAc (pH 5.0)/1 mM EDTA/1 mM dithiothreitol.

The fusion protein solution was then applied to a 4x10 cm CM-Sepharose (Pharmacia) column equilibrated with the same buffer. The fusion protein was eluted with a linear gradient formed with 500 ml of 8M urea/25 mM Tris-HOAc pH 5.0/1 mM EDTA/1 mm dithiothreitol and 500 ml of the same buffer with 0.2M NaCl. The fusion protein was further purified on a 5x60 cm Sephacryl S-200 column equilibrated with 5M guanidine-HCl/50 mM Tris-HCl/1 mM EDTA/1 mM dithiothreitol to remove any trace of impurities. The combined fraction was extensively dialyzed against 50 mM Tris-HCl (pH 8.0)/0.5M urea/1 mM $CaCl_2$.

Protein Cleavage

The cIIFX beta FX alpha-globin or cIIFX beta-globin fusion protein was incubated at 0° C. with blood coagulation factor $X_a$ that had been activated with Russell's viper venom immobilized on cyanogen bromide-activated Sepharose-6B. 100 micro 1 aliquots were removed after intervals of 2, 5, 15, 30, 60 and 120 minutes. 100 ul of protein sample buffer (Laemmli, 1970) and 1 ul of 100 mM DTT were added to each aliquot, which was then boiled before being applied to an SDS polyacrylamide gel. Factor $X_a$ cutting of the cIIFX beta FX alpha fusion protein gives rise to a number of polypeptide products. This is due to the presence of two recognition sites within the protein. Complete digestion releases three polypeptides, a cII protein fragment and a beta-globin fragment both with the tetrapeptide Ile—Glu—Gly—Arg (SEQUENCE:16) the carboxyl terminus, and the desired alpha-globin. Partial digestion of the fusion protein gives two other products.

Factor Xa cleavage of cIIFX-beta yields two products, a cII fragment and the desired beta globin.

Formation of Semi-Artificial Hb with alpha-globin produced in *E.coli*

25 mg of hemin-Cl was dissolved in 2.5 ml of 0.1N KOH and 30 diluted with 20 ml of water and 2.5 ml of 1M KCN.

The native beta chain was diluted in 20 mM K phosphate buffer pH 5.7, 1 mM EDTA, 1 mM dithiothreitol (DTT) and bubbled with CO. Alpha globin produced in *E.coli* was dissolved in 8M urea/50 mM Tris-Cl pH 8/1 mM EDTA/1 mM DTT at the concentration of 5 mg/ml and incubated at room temperature for 3 hours. The alpha-globin solution was added dropwise to 20 volumes of 30 mM K phosphate buffer pH 5.7, 1 mM EDTA, 1 mM DTT with gentle stirring. The hemin-dicyanide solution (1.2 equivalent to the alpha-globin) was added dropwise to the alpha-globin solution and the beta chain was added in slight excess. The semi-artificial Hb was dialyzed overnight against 0.1M K phosphate pH 7.6 1 mM EDTA, 1 mM KCN.

Formation of semi-artificial Hb with betaglobin produced in *E.coli*

Beta-globin (100 mg) was dissolved in 8M urea, 50 mM Tris-Cl pH 8.0, 1 mM DTT, 1 mM EDTA at the concentration of 5 mg/ml and incubated at room temperature for 1 hr. The beta-globin solution was added dropwise to 16 volumes of alpha chain solution (either isolated from Hgb A, or produced by recombinant means) (3.2 mg/ml) in 10mMTris-Cl pH 8.0. The hemin-dicyanide solution (1.2 equivalents to beta-globin) was added dropwise with gentle stirring. The semi-artificial Hb was dialyzed against 2 changes of 0.1M K phosphate pH 7.4 1 mM EDTA, 1 mM KCN.

Formation of wholly artificial hemoglobin

The lyophilized recombinant alpha and beta globins were dissolved in 8M urea/50 mM Tris-Cl, pH 8.0/1 mM EDTA/1 mM DTET, diluted to a concentration of 5 mg/ml and incubated at room temperature for 3–4 hours. The alpha globin was then diluted to 0.3 gm/ml with chilled 20 mM $K_2HPO_4$, pH 5.7/1 mM EDTA/1 mM DTT. Hemin (25 mg) was dissolved in 2.4 mg 0.1M KOH, diluted with an equal volume of 1M KCN; this solution was then made 0.1 mg.ml in hemin and 20 mM $K_2HPO_4$, pH 6.7 with stock phosphate buffer. Hemin from this solution was added to a 2.8 molar excess to chilled alpha-globin; and equal molar amount of beta-globin was added and the solution was dialyzed at 4° C. overnight against 0.1M $K_2HPO_4$, pH 7.6/1 mM EDTA/1 mM KCN.

Purification of the semi-artificial or wholly artificial Hb

The artificial Hb was concentrated by ultra-filtration using diaflo PM-10 membrane (Amicon) and transferred into a 200 ml screw-top test tube with a rubber septum. The hemoglobin solution was deoxygenated by evacuation and flushing with $N_2$, and then the solution was saturated with CO. 100 mM Sodium dithionite solution was prepared anaerobically in a 20 ml screw-top test tube with rubber septum. 4.5 equivalents of dithionite were added to the Hb solution with a syringe, and the mixture incubated on ice for 15 min.

The Hb solution was gel-filtered against 10 mM Na phosphate buffer pH 6.0 on a 4×40 cm Sephadex G-25 (fine) column. The Hb was then applied to a 2×10 cm CM-52 (Whatman) column equilibrated with the same buffer and the chromatography was developed with a linear gradient of 500 ml 10 mM Na phosphate buffer pH 6.0 and 500 ml of 70 mM sodium phosphate buffer pH 6.9. CO was removed from Hb by photolysis under a stream of oxygen. This Hb shows native oxygen binding properties.

A wholly artificial hemoglobin may be prepared by the combination of alpha-globin and beta-globin both produced in *E.coli*, or any other host of a non-erythroid nature, with a source of heme.

EXAMPLE 2

Production of Low-Affinity Hemoglobin Mutants

Construction and Mutagenesis of pLCIIFXbeta-globin(Thr[102])

A synthetic oligonucleotide of sequence dGGAGCCT-GAAAGTCTCAGGA [SEQ ID:18] was designed from published mRNA sequence information [Bunn & Forget, eds., *Hemoglobin: Molecular, Genetic and Clinical Aspects*, W. B. Saunders Co., Philadelphia, Pa., 169–222 (1986)] and synthesized on a controlled glass support. The oligonucleotide was gel purified [Lloyd et al., *BioTechniques* 4, 8–10 (1986)] and used to prime the site-specific mutagenesis of M13 mp10 cIIFXbeta-globin by the methods of Zoller and Smith [*Methods in Enzymology* 100, Academic Press, New York, 468–500 (1983)].

The mutagenic oligonucleotide was complementary to the beta-chain structural gene sequence flanking and centered upon the wild-type codon for Asn[102]. At this triplet specific base substitutions were designed into the oligonucleotide to specify ACT-Thr[102], the amino acid sequence alteration which is characteristic of the Kansas beta-globin mutant [Bonaventura & Riggs, i J. Biol. Chem. 243, 980–991 (1968)]. The particular Thr codon employed in this substitution, while differing from that found in the original Kansas isolate (Bonaventura and Riggs, supra), is preferentially utilized in highly expressed *E. coli* genes [Grantham et al., *Nucleic Acids Res.* 9, r43–r74 (1981)].

Production of Mutant beta-Globin

The products of the in Vitro mutagenesis reaction were transformed into competent *E. coli* $^M$Z-1 [galK$_{am}$8attL BAmN$_7$N$_{53}$cI857 H1, his⁻, ilv⁻, bio⁻, N⁺, a gift of Dr. K McKenney and available on request from the Medical Research Council), by standard procedures of $CaCl_2$-shock [Maniatis et al., *Molecular Cloning*, Cold Spring Harbor Laboratory, New York, 250–251 (1982); Nagai & Thogersen, *Methods in Enzymology*, supra].

Transformants harboring the desired mutant M13 bacteriophage constructs were then identified by differential plaque-hybridization screenings at high stringency using gamma[³²P]-end-labeled oligonucleotides as probes.

The reactants used to prepare each of the phosphorylated hybridization probes were 300 pM (2 ug) of oligonucleotide, 100 pM (0.7 mCi) gamma-[$^{32}$P]-ATP (specific activity approximately 6000 Ci/mM), and 15 units T4 polynucleotide kinass in a total reaction mixture of 50 ul. After 37° C. incubation for 2 h, the end-labeled oligomers were purified away from orthophosphate and unincorporated precursor nucleotide using reverse phase C-18 sep-paks (Waters Associates Milford, Mass.). This latter procedure involved loading the phosphorylation reaction mixture onto the C-18 cartridge in an aqueous salt solution, eluting orthophosphate and unincorporated ATP with water followed by 10% methanol, and then eluting the purified oligomer with 60% methanol. The probes employed comparatively in the differential hybridization analyses were both the mutagenic oligonucleotide an another 20-mer (dGGAGCCTGAAGTTCTCAGGA) (SEQUENCE ID:19) which is perfectly complementary to the wild-type beta-Chain DNA sequence in the same coding region.

After identification and plaque purification (Zoller & Smith, supra) of several of the desired M13 phage constructs, one of the resultant Thr$^{102}$ mutants, termed M13 mp10 cIIFX beta-globin (Thr$^{102}$), was further verified by DNA sequence analysis [Sanger et al., *Proc. Natl. Acad. Sci. USA* 74, 5463–5467 (1977)] to contain the desired mutation at codon-102, and only that particular amino acid sequence alteration in the beta-chain structural gene coding sequence.

A large scale preparation of M13 mp10 cIIFX -beta-globin(Thr$^{102}$) RF DNA was conducted as follows [Recinos, Ph.D. Dissertation, Vanderbilt University (1987)]. The host *E. coli* was grown at 37° C. overnight in M9 minimal medium (Maniatis et al., supra) plus 2 ug/ml thiamine. 0.3 ml of this cell culture was then diluted (1:50) into 14.7 ml 2X YT medium and growth at 37° C. was continued for an additional 2 h. The latter culture was again diluted (1:10) into a final volume of 150 ml 2X YT, and this cell solution was inoculated with the plaque purified mutant M13 phage construct at a multiplicity of infection of approximately one. This phage infection was then shaken vigorously at 37° C. for 14 h, and cells for RF preparation were harvested by centrifugation (5000×g, 10 min, 4° C.). The mutant phage supernatant was stored at −20° C. for use in scaled-up versions of the protocols (Zoller & Smith, supra) for phage purification and for single-stranded template preparation.

Double-stranded RF DNA was purified from the cell pellets as follows. Pellets were frozen in an alcohol dry-ice bath for 10 min, thawed at 20° C. and completely resuspended on ice in 10 ml 25% sucrose, 50 mM Tris-HCl (pH 8.0). Lysozyme was added to a final concentration of 4 mg/ml, and incubation was continued on ice for 5 min. EDTA was then added to a final concentration of 80 mM, and again after 5 rain on ice, an equal volume of 0.5% Triton X-100, 50 mM Tris-HCl (pH 8.0), 62.5 mM EDTA was added. This solution was kept on ice for 15 min more, and then 5M NaCl was added to a final concentration of 1M. The last solution was loaded into Beckman Type 70 Ti rotor bottles, and after a further incubation on ice for 3 h, was centrifuged at 40,000 rpm for 75 min at 15° C. RF DNA was decanted with the supernatant and precipitated at −20° C. for 20 min with the addition of an equal volume of isopropanol. DNA precipitates were pelleted and resuspended in 10 mM Tris-HCl (pH 8.0), 1 mM EDTA, 100 mM NaCl, and treated with RNase (final conc. 100 ug/ml) for 2 h at 37° C. This solution was phenol and chloroform extracted (one time each), and the DNA was ethanol precipitated and resuspended in 30 ml 10 mM Tris-HCl (pH 8.0), 1 mM EDTA. The DNAs were twice banded by CsCl-ethidium bromide density gradient equilibrium centrifugation. Form I DNA bands were extracted 4X with CsCl-saturated isopropanol to remove ethidium bromide, and DNA and CsCl were ethanol precipitated. CsCl was removed from DNA pellets by resuspension in and dialysis against 10 mM Tris-HCl (pH 8.0), 0.2 mM EDTA. A final ethanol precipitation and resuspension in 0.5 ml Tris-HCl (pH 8.0) yielded 150 ug of purified M13 mp10 cIIFXbeta-globin(Thr$^{102}$) RF DNA for use in subcloning the mutant beta-globin structural gene into the beta-globin expression construct.

The mutated beta-chain sequence was moved into the beta-chain expression vector, pLcIIFXbeta-globin (nic$^-$), by the following procedures. Mutant clone RF (50 ug) was restriction enzyme digested with Sac I and Hind III, and the resultant cIIFXbeta-globin (Thr-102) fragment was isolated from a 1% preparative agarose gel (Maniatis et al., supra) and gel-purified by a phenol freeze-thaw procedure [Benson, *BioTechniques* 2, 77–78 (1984)]. Approximately 200 ug of expression vector DNA was isolated and purified from *E. coli* QY13 transformant cell pellets by methods nearly identical to those described above for the Rf preparation. This plasmid DNA (20 ug) was similarly restricted with Sac I and Hind III and further treated with bacterial alkaline phosphatase (Bethesda Research Laboratories, Gaithersburg, Md., as directed) to remove the 5' phosphates from the vector DNA, thereby preventing recircularization without insert DNA in subsequent ligation reactions.

The purified mutant insert DNA fragment was then ligated back into the expression construct at moderate insert end-concentration, replacing the wild-type protein coding sequences previously therein. Ligation reaction conditions (modified from procedure of New England Biolabs, Inc., Beverly, Mass.) were: 11 ug vector DNA and 2.1 ug purified-insert DNA in 50.0 mM Tris-HCl (pH 7.8), 100 mM MgCl$_2$, 6 mM ATP, 2 mM dithiothreitol; total reaction volume=125 ul. Incubation for the ligation was at 16° C. for 10 h. The final ligation reaction mixture was used to transform competent *E. coli* QY13 with selection for ampicillin resistance. Transformants harboring the desired plasmid construct for the expression of mutant beta-chain were identified by differential colony hybridization screenings [Grunstein & Hogness, *Proc. Natl. Acad. Sci. USA* 72, 3961–3965 (1975), with modifications] using the end-labeled mutagenic and wild-type oligonucleotides described above as probes. The correct plasmid construct was further verified by restriction analysis and by its expression of a protein which is chromatographed differentially from the wild-type cIIFX beta-globin fusion product by HPLC. The mutant beta-globin was produced, purified and combined with alpha-globin as described for native beta-globin.

Construction and Mutagenesis of pLcIIFXbeta-globin(Ile$^{67}$)

Mutation of the val$^{67}$codon was introduced into the beta-globin cDNA sequence in M13 mp10 cIIFXbeta-globin using the mutagenic primer (dGCACCGAGGATTTTCTTGCC) (SEQUENCE ID:19) as above. The mutant beta-globin was produced, purified and combined with alpha globin as described for native beta-globin to obtain a mutant hemoglobin.

Construction and Mutagenesis of pLcIIFXbeta-globin(phe$^{63}$)

Mutation of the his$^{63}$ codon was introduced into the beta-globin cDNA sequence in M13 mp10 cIIFXbeta-globin using the mutagenic primer (dTTCTTGCCGAAAGCCTTCA) [SEQ ID:20] as above. The mutant beta-globin was produced, purified and combined with alpha globin as described for native beta-globin to obtain a mutant hemoglobin.

Characterization of Mutant Hemoglobin

Oxygen equilibrium studies for Hgb (beta phe$^{63}$) Hgb (beta ile$^{67}$) were performed in 0.05M bis-Tris pH 7.4, 0.1M NaCl, at 25° C. using the automated recording apparatus of K. Imai (Meth. Enz. 76, 438–449, 1981) and for Hgb (beta thr$^{102}$) in 0.1M HEPES pH 7.4, 0.1M NaCl using a thin layer optical cell (Gill, S. J. Meth. Enz. 76, 427–438, 1981). Results are shown in Table 3.

EXAMPLE 3

Blood Substitute Solution

The purified hemoglobin is incorporated into a physiologically acceptable blood substitute solution. A preferred solution includes the following components:

| | |
|---|---|
| Hgb(gm/l) | 60–120 |
| Sodium(mEq/l) | 135–145 |
| Potassium(mEq/l) | 3.5–4.5 |
| Chloride(mEq/l) | 90–110 |

Preferably, the solution has a pH of 7.3–7.5, an osmolality of 280–310, and an oncotic pressure of 20–30 mm Hg. Osmolality is controlled by concentration of hemoglobin and of the electrolytes, as well as by the optional ingredient glucose (preferably 0–30 g m/l). The oncotic pressure is controlled by the concentration of the hemoglobin and by its degree of crosslinking. Agents, such as albumin (0–70 gm/l), dextran (0–100gm/l) and polyethylene glycol (0–25 gm/l) may be added to increase oncotic pressure. Moreover, to reduce the degree of methemoglobin formation, anti-oxidant or free radical scavengers, such as mannitol (0–20 gm/l), glutathione (0–4 gm/l), ascorbic acid (0–0.3 gm/l) and vitamin E (0–100 IU/l) may be provided.

If a low oxygen affinity mutant hemoglobin is employed, it may be desirable or necessary to adjust the $P_{50}$ of the solution to the preferred level by suitable choice of electrolytes, pH and other characteristics of the composition. Preferably, the final solution has a $P_{50}$ of 24–32 torr under standard physiological conditions.

EXAMPLE 4

Preparation of Cys Substitution Mutants of Alpha and Beta Globin

Standard techniques of molecular biology according to Maniatis et al. (5) were used throughout.

Subcloning of haemoglobin genes

Hoffman, et al., Ser. No. 07/349,623, filed May 10, 1989, incorporated by reference, describes the cloning of alpha and beta globin genes into the commercially available plasmid pKK223 (Pharmacia/LKB, Piscataway, N.J.). The resulting expression vector served as a convenient source of the genes and was cleaved with HindIII and SmaI to excise the 1016 base pair fragment carrying the genes. However, the alpha and beta globin genes could have been obtained from any convenient source. The genes were isolated from the vector DNA using Geneclean (Bio 101, Inc.) and ligated into the high copy plasmid pUC9 which had been linearized at its multiple cloning site. The newly constructed vector (pCHB) was then transformed into DH5e competent cells (BRL). Positive transformants were identified by restriction analysis. The plasmid resulting was used as the basis of all subsequent mutagenic constructs.

Mutagenesis of the hemoglobin genes

The same basic technique was used for the modification of each codon. To avoid repetition only the mutagenesis of codon 97 beta will be described in detail here.

To mutate each codon, two oligonucleotides were required that were complementary to each other, and were identical to the wild-type sequence except save for the missense mutations necessary to alter the codon specified. A list of the oligonucleotides used is given in Table 5 (SEQ ID:21–SEQ ID:28). Each oligonucleotide was designed to create a double-stranded sequence after annealing to its complementary sequence, of 51–55 base pairs in length. In addition, each double-stranded oligonucleotide created the appropriate "sticky end" at its 5' and 3' extremities to facilitate its ligation into the relevant gene for successful mutagenesis. For example, to modify the codon 94 it was necessary for the double stranded'sequence to exhibit the "sticky end" of an MluI digestion at its 5' end and a HpaI "blunt end" at its 3' end. Since the other three codons mutagenized were localized within a small region of the beta gene, each mutagenic double stranded oligonucleotide displayed a CaCI "sticky end" at its 5' end and a SpeI "sticky end" at its 3' end. All oligonucleotides used in this work (and in the subsequent sequencing step) were synthesized on an Applied Biosystems oligonucleotide synthesizer.

With such large oligonucleotides, it was important to purify them prior to use. Consequently, the 97 beta sense (55mer) and 97 beta antisense (63mer) oligonucleotide were separated from the prematurely terminated oligonucleotide fragments on an 8M urea/12% polyacrylamide gel. The appropriate bands were then excised, purified, and quantified at 260 nm.

The sense and antisense oligonucleotides were then phosphorylated with T4 polynucleotide kinase before equimolar amounts of each were annealed together. pCHB DNA was double-digested with SacI and SpeI and isolated using Geneclean. Finally, the mutagenic double-stranded oligonucleotide was ligated into the linearized pCHB vector, and then transformed into DH5α competent cells.

Restriction analysis was used initially to identify putative transformants which were then more extensively analyzed via plasmid sequencing. The Sequenase kit (United States Biochemicals) was used to carry out the DNA sequencing. Sequencing of the whole of the 1 kb globin gene sequences required the design and synthesis of a number of oligonucleotide primers (Table 6) [SEQ ID:29–SEQ ID:34]. These were used in addition to the Universal primer and the reverse Universal primer (Table 6) which allowed the extremes of the insert to be sequenced. Having identified a positive mutant the clone was named pCHB0097. With the construction of the mutant pCHB4400 (containing the mutagenized codon 44α), it only remained to subclone the 512 bp PstI - HindIII fragment of pCHB0097 (with the abberrant gene) into the identically digested vector pCHB4400 before the final construct, containing both mutagenized alpha and beta genes, was created. This clone was designated pCHB4497. The success of this step was confirmed by both restriction and sequence analysis. The same protocol was then repeated for all the other mutants subsequently constructed.

References for Example 4

1. Perutz, M. F. (1979). Ann. Rev. Biochem. 48, 327–386.
2. Nagai, K., Perutz, M. F., Poyart, C. (1985). Proc. Natl. Acad. Sci. (USA). 82, 7252–725.5.
3. Fermi, G., Perutz, M. F., Shaanan, B., Fourme, .R (1984). J. Mol. Biol. 175, 159–174.
4. Shaanan, B. (1983). J. Mol. Biol. 171, 327–386.
5. Maniatis, T., Fritsch, E. F., Sambrook, J. (1982). In Molecular Cloning: A Laboratory Manual (Cold Spring Harbor Lab., Cold Spring Harbor, N.Y.).

EXAMPLE 5

Production of Recombinant Hemoglobin and Conversion to Disulfide Cross-Linked Hemoglobin Hoffman, et al., Ser. No. 07/349,623, incorporated by reference herein, describes the coexpression of alpha and beta globins and the in vivo assembly of hemoglobin from the expression products. Our method was identical to that described by Hoffman, et al., Ser. No. 07/349,623 except for the use of differently mutated alpha and beta globin genes.

In brief, we constructed an artificial polycistronic operon comprising a Tac promoter, a short cistron described in Sohoher, et al., Meth. Enzymol., 153:401–16 (1987), the mutant alpha globin gene, an intercistronic region, the "Schoner cistron" again, and the mutant beta globin gene.

To express recombinant Hgb that could form intra-subunit disulfide bonds, the gene sequence containing alpha$^{44}$-cys/beta$^{97}$-cys needed to be cloned back into the pKK-223 expression plasmid. pCHB4497 was restriction digested with SmaI and HindIII and the approximately 1kb fragment containing the alpha/beta globin genes isolated by electrophoresis and Geneclean. This fragment was then cloned into SmaI and HindIII cut pKK-223 with T4 ligase. *E. coli* were transformed with this ligation mixture and individual clones were isolated. Plasmid containing the alpha$^{44}$-cys/beta$^{97}$-cys genes in the pKK-223 expression system was identified as pHB-cysα44β97.

*E. coli* were transformed with the plasmid pHB-cysα44β97. Two liters of TB medium containing ampicillin (100 μg/ml) was inoculated with 20 mL of an overnight culture of the *E. coli* clone, and grown to an optical density at 600 nm (OD$_{600}$) of 2.1 at 37° C. The culture was induced with IPTG (2.5 mM final concentration) and grown to an OD$_{600}$ of 3.5.

The cells (40 gm) were collected by centrifugation at 10,000×g and suspended in 80 mL of lysis buffer (50 mM Tris-HCl, pH 8.0, 25% sucrose, 1 mM EDTA). Ten milliliters of lysozyme solution (18 mg/ml in lysis buffer) was added and the mixture incubated on ice for 30 min. MgCl$_2$, MnCl$_2$, and DNAse I (Sigma, St. Louis, Mo.) were added to final concentrations of 10 mM, 1 mM and 10 μg/mL, respectively. The cells were incubated at room temperature for 1 hour and an equal volume of a solution containing 1% one percent deoxycholic acid, 1% Nonidet P-40, 20 mM Tris-HCl pH 7.5, 2 mM EDTA was added to the lysate.

Particulate material was removed by centrifugation at 10,000×g for 10 min. The pH of the supernatant was adjusted to 6.0 and the supernant was loaded onto a CM-cellulose column (2.5×15 cm) equilibrated in 10mMNAPO$_4$, pH 6.0 at 4° C. The column was washed with two bed volumes of 10 mM NaPO$_4$, pH 6.0 followed by a linear gradient of 10 mM NaPO$_4$, pH 6.9 to 20 mM NaPO$_4$, pH 9.0 (400 mL total volume). Fractions containing a red (oxyhemoglobin) solution were combined; an aliquot of this solution was scanned from 650 nm to 400 nm revealing a spectrum identical to that for oxyhemoglobin. An aliquot of the same peak was analyzed by SDS-PAGE electrophoresis with hemoglobin as molecular weight standard and was found to contain two protein bands migrating with native alpha and beta globin. The purified recombinant Hgb (alpha$^{44}$-cys/beta$^{97}$-cys) was found to have an optical spectrum identical to that of oxy-hemoglobin. The mutant Hgb was tested for titratable cysteine residues using p-hydroxymercuribenzoate according to the procedure of Boyer, P. (J. Amer. Chem. Soc. 1954, 76, 4331) and found to have 6.2 moles titratable cysteines/mole Hgb; Hgb Ao contained 2.2 moles titratable cysteines/mole Hgb under identical conditions. This result confirms that Hgb is being produced with additional cysteine residues. The Hgb solution was deoxygenated by flushing with dry N$_2$ gas to approximately 1torr pO$_2$, tightly stoppered and stored at 4° C. The solution was periodically sampled under deoxy conditions and assayed for tittable cysteine residues. After 72 hours the cysteine-containing Hgb solution contained only 2.5 moles titratable cysteines/mole Hgb, nearly identical to that of a solution of Hgb A$_o$ (2.2 moles titratable cysteines/mole Hgb). The loss of active cysteines indicates that upon standing in the deoxy, or T state, the molecule has formed disulfide bonds.

TABLE 1

NATURAL LOW AFFINITY HEMOGLOBIN MUTANTS

| Hemoglobin | Alpha Mutant | P$_{50}$* RBC-Free Hgb | Whole Blood(nl) | Area of Mutant | Reference |
|---|---|---|---|---|---|
| Hirosaki | 43(CD1) phe-->leu | n/a | | heme | 1,2 |
| Torino | 43(CD1) phe-->val | n/a | | heme | 1,3 |
| Moabit | 86(F7) leu-->arg | | 30.6(26.4–29.2) | heme | 4 |
| Titusvitte | 94(G1) asp-->asn | 15.8(4.7) | | α$_1$β$_2$ | 5 |

| Hemoglobin | Beta Mutant | P$_{50}$(mmHg) Hgb(nl) | Whole Blood(nl) | Area of Mutant | Reference |
|---|---|---|---|---|---|
| Raleigh | 1 val-->acetyl ala | 4.0(2.2) | | DPG site | 6 |
| Connecticut | 21(B3) asp-->gly | 5.0(2.2) | | B-E helices | 7 |
| Moscva | 24(B6) gly-->asp | 14.8(12.6) | | B-E helices | 8 |
| Rothschild | 37(C3) trp-->arg | 3.5(2.0) | | α$_1$β$_2$ | 9 |
| Hazebrouck | 38(C4) thr-->pro | | 36(27–29) | α$_1$β$_2$ | 10 |
| Hammersmith | 42(CD1) phe-->ser | n/a | | heme/α$_1$β$_2$ | 1,11 |
| Louisville | 42(CD1) phe-->leu | 24(21) | | heme/α$_1$β$_2$ | 12,13 |
| Sendagi | 42(CD1) phe-->val | 3.75(3.05) | | heme/α$_1$β$_2$ | 14 |
| Cheverley | 45(CD4) phe-->ser | | 38.7(28.7) | heme | 15 |
| Okaloosa | 48(CDT) leu-->arg | 0.95(0.7) | 30(26) | C-D helices | 16 |
| Bologna | 61(E5) lys-->met | | 37.6(27.0) | B-E helices | 17 |
| Cairo | 65(E9) lys-->gln | | 41(31) | heme | 18 |
| Chico | 66(E10) lys-->thr | 10.1(5.0) | 38.0(27.2) | heme | 19 |
| Bristol | 67(E11) val-->asp | | 25.0(19.0) | heme | 20 |
| Seattle | 70(E14) ala-->asp | | 43.5(28.1) | heme | 21,22 |
| Vancouver | 73(E17) asp-->tyr | n/a | | | 1.23 |
| Korle-Bu | 73(E17) asp-->asn | n/a | | | 1,24 |
| Mobile | 73(E17) asp-->val | n/a | | | |

TABLE 1-continued

NATURAL LOW AFFINITY HEMOGLOBIN MUTANTS

| | | | | | |
|---|---|---|---|---|---|
| Rahere | 82(EF6) lys-->thr | 15.5(11.0) | | DPG site | 26 |
| Pyrgos | 83(EF7) gly-->asp | | | External | 27 |
| Roseau-Pointe | 90(F6) glu-->gly | | 38(28) | $\alpha_1\beta_2$ | 28 |
| Agenogi | 90(F6) glu-->lys | 9.0(6.8) | | $\alpha_1\beta_2$ | 29 |
| Caribbean | 91(F7) leu-->arg | 28.0(21.0) | | heme | 30 |
| Kansas | 102(G4) asn-->thr | 28.0(9.0) | | $\alpha_1\beta_2$ | 31 |
| Beth Israel | 102(G4) asn-->ser | | 88.0(26.0) | $\alpha_1\beta_2$ | 32 |
| Saint Mande | 102(G4) asn-->tyr | | 52(28) | $\alpha_1\beta_2$ | 33 |
| Richmond | 102(G4) asn-->lys | n/a | | heme | 1,34 |
| Burke | 107(G9) gly-->arg | 9.3(7.7) | | heme | 35 |
| Yoshizuka | 108(G10) asn-->asp | 12.9(9.0) | | $\alpha_1\beta_2$ | 36 |
| Presbyterian | 108(G10) asn-->lys | 6.3(2.5) | | $\alpha_1\beta_2$ | 37 |
| Peterborough | 111(G13) val-->phe | 14.0(9.0) | | $\alpha_1\beta_2$ | 38 |
| New York | 113(G15) val-->glu | n/a | | G-helix | 1,39 |
| Hope | 136(H14) gly-->asp | n/a | | heme | 1,40 |
| Himeji | 140(H18) ala-->asp | 5.8(4.5) | | | |

*Parenthetical values are that investigator's measured $P_{50}$ for conventional Hgb A in RBC-free or RBC-bound state, as indicated

REFERENCES FOR TABLE 1

1) *Hemoglobin* 1987, 11, 241–308.
2) Ohba, Y.; Miyaji, T.; Matsuoka, M.; Yokoyama, M.; Numakura, H.; Nagata, K.; Takebe, Y.; Izumu, Y.; Shibata, S. *Biochemi. Biophys. Acta* 1975, 495, 155–160.
3) Beretta, A.; Prato, V.; Gallo, E.; Lehmann, H. *Nature* 1968, 217, 1016–1018.
4) Knuth, A.; Pribilla, W.; Marti, H. R.; Winterhalter, K. H. *Acta Haematol* 1979, 61, 121–124.
5) Schneider, R. G.; Atkins, R. J.; Hosty, T. S.; Tomlin, G.; Casey, R.; Lehmann, H.; Lorkin, P. A.; Nagei, K. *Biochem Biophys. Acta* 1975, 400, 365–373.
6) Moo-Penn, W. F.; Bechtel, K. C.; Schmidt, R. M.; Johnson, M. H.; Jue, D. L.; Schmidt, D. E.; Dunlap, W. M.; Opella, S. J.; Boneventura, J.; Boneventura, C. *Biochemistry* 1977, 16, 4872–4879.
7) Moo-Penn, W. F.; McPhedran, P.; Bobrow, S.; Johnson, M. H.; Jue, D. L.; Olsen, K. W. *Amer. J. Hematol* 1981, 11, 137–145.
8) Idelson, L. I.; Didkowsky, N. A.; Casey, R.; Lorkin, P. A.; Lehmann, H. *Nature* 1974, 249, 768–770.
9) Gacon, G.; Belkhodja, O.; Wajcman, H.; Labie, D. *Febs Lett* 1977, 82, 243–246.
10) Blouquit,; Delanoe,-Garin, J.; Lacombe, C.; Arous, N.; Cayre, Y.; Peduzzi, J.; Braconnier, F.; Galacteros, F.; *Febs Lett.* 1984, 172, 155–158.
11) Dacie, J. V.; Shinton, N. K.; Gaffhey, P. J.; Carrell, R. W.; Lehmann, H. *Nature* 1967, 216, 663–665.
12) Keeling, M. M.; Ogden, L. L.; Wrightstone, R. N.; Wilson, J. B.; Reynolds, C. A.; Kitchens, J. L.; Huisman, T. H. *J. Clin. Invest.* 1971, 50, 2395–2402.
13) Bratu, V.; Larkin, P. A.; Lehmann, H.; Predescu, C. *Biochem. Biophys. Acta.* 1971, 251, 1–6.
14) Ogata, K.; Ho, T.; Okazaki, T.; Dan, K.; Nomura, T.; Nozawa, Y.; Kajita, A. *Hemoglobin* 1986, 10, 469–481.
15) Yeager, A. M.; Zinkham, W. H.; Jue, D. L.; Winslow, R. M.; Johnson, M. H.; McGuffey, J. E.; Moo-Penn, W. F. *Ped. Res.* 1983, 17, 503–507.
16) Charache, S.; Brimhall, B.; Milner, P.; Cobb, L. *J. Clin. Invest.* 1973, 52, 2858–2864.
17) Marinucci, M.; Giuliani, A.; Maffi, D.; Massa, A.; Giampolo, A.; Mavilio, F.; Zannotti, M.; Tantori, L. *Biochem. Biophys. Acta.* 1981, 668, 209–215.
18) Garel, M. C.; Hasson, W.; Coquelet, M. T.; Goosens, M.; Rosa, J.; Arous, N. *Biochem. Biophys. Acta.* 1976, 420, 97–104.
19) Shih, D. T.; Jones, R. T.; Shih, M. F. C.; Jones, M. B.; Koler, R. D.; *Hemoglobin* 1987, 11, 453–464.
20) Steadman, J. H.; Yates, A.; Huehns, E. R.; Brit., J. *Haematol* 1970, 18, 435–446.
21) Stamotoyannopoulos, G.; Parer, J. T.; Finch, C. *New Eng. J. Med.* 1969, 281, 915–919.
22) Anderson, N. L.; Perutz, M. F.; Stamatoyannopoulos, G. *Nature New. Biol.* 1973, 243, 275–276.
23) Jones, R. T.; Brimhall, B.; Pootrakul, S.; Gray, G. *J. Mol. Evol.* 1976, 9, 37–44.
24) Konotey-Ahulu, F. I. D.; Gallo, E.; Lehmann, H.; Ringelhann, B. *J. Med. Genet.* 1968, 5, 107–111.
25) Schneider, R. G.; Hosty, T. S.; Tomlin, G.; Atkins, R.; Brimhall, B.; Jones, R. T. *Biochem Genet.* 1975, 13, 411–415.
26) Sugihara, J.; Imamura, T.; Nagafuchi, S.; Boneventura, J.; Boneventura, C.; Cashon, R. *J. Clin. Invest.* 1985, 76, 1169–1173.
27) Tatsis, B.; Sofroniadou, K.; Stergiopoulas, C. I. *Blood* 1976, 47, 827–832.
28) Merault, G.; Keclard, L.; Saint-Martin, C.; Jasmin, K.; Campier, A.; Delanoe Garin, J.; Arous, N.; Fortune, R.; Theodore, M.; Seytor, S.; Rosa, J.; Blouquit, Y.; Galacteros, F. *Febs Lett.* 1985, 184, 10–13.
29) Imar, K.; Morimoto, H.; Kotani, M.; Shibata, S.; Miyaji, T.1 Matsutomo, K. *Biochem. Biophys. Acta.* 1970, 200, 197–202.
30) Ahern, E.; Ahern, V.; Hilton, T.; Serjeant, G. D.; Serjeant, B. E.; Seakins, M.; Lang, A.; Middleton, A.; Lehmann, H. *Febs Lett.* 1976, 69, 99–102.
31) Boneventura, J.; Riggs, A.; *J. Biol. Chem.* 1968, 243, 980–991.
32) Nagel, R .L.; Lynfield, J.; Johnson, J.; Landeau, L.; Bookchin, R. M.; Harris, M. B. *N. Eng. J. Med.* 1976, 295, 125–130.
33) Arous, N.; Braconnier, F.; Thillet, J.; Blouquit, Y.; Galacteros, F.; Chevrier, M.; Bordahandy, C.; Rosa, J. *Febs Lett.* 1981, 126, 114–116.
34) Efremov, G. D.; Huisman, T. H. J.; Smith, L. L.; Wilson, J. B.; Kitchens, J. L.; Wrightston, R. N.; Adams, H. R.; *J. Biol. Chem.* 1969, 244, 6105–6116.
35) Turner, J. W.; Jones, R. T.; Brimhall, B.; DuVal, M. C.; Koler, R. D. *Biochem. Genet.* 1976, 14, 577–585.
36) Imamura, T.; Fujita, S.; Ohta, Y.; Hanada, M.; Yanase, T. *J. Clin. Invest.* 1969, 48, 2341–2348.
37) Moo-Penn, W. F.; Wolff, J. A.; Simon, G.; Vacek, M.; Jue, D. L.; Johnson, M. H. *Febs Lett.* 1978, 92, 53–56.
38) King, M. A. R.; Willshire, B. G.; Lehmann, H.; Marimoto, H. *Br. J. Haem.* 1972, 22, 125–134.
39) Ranney, H. M.; Jacobs, A. S.; Nagel, R. L. *Nature* 1967, 213, 876–878.

40) Minnich, V.; Hill, R. J.; Khuri, P. D.; Anderson M. E. *Blood* 1965, 25, 830–838.
41) Ohba, Yj; Miyaji, T.; Murakami, M.; Kadowaki, S.; Fujita, T.; Oimoni., M.; Hatanaka, H.; Ishikawa, K.; Baba, S.; Hitaka, K,; Imai, K. *Hemoglobin* 1986, 10, 109–126.

Table 2: Candidate Non-Naturally Occurring Low Affinity Hemoglobin Mutants alpha chain
46 phe≧thr
46 phe≧ser
46 phe≧ala
58 his≧phe
58 his≧trp
61 lys≧thr
61 lys≧ser
61 lys≧met
61 lys≧asn
62 val≧leu
62 val≧ile
62 val≧phe
62 val≧trp
65 ala≧asp
94 asp≧gln
94 asp≧thr
94 asp≧ser
94 asp≧lys
94 asp≧gly
94 asp≧arg
beta chain
21 asp≧ala
21 asp≧ser
45 phe≧ala
45 phe≧thr
45 phe≧val
63 his≧phe
63 his≧trp
66 lys≧ser
66 lys≧asn
67 val≧phe
67 val≧trp
67 val≧ile
70 ala≧glu
70 ala≧ser
70 ala≧thr
96 leu≧phe
96 leu≧his
96 leu≧lys
98 val≧trp
98 val≧phe
102 asn≧asp
102 asn≧glu
102 asn≧arg
102 asn≧his
102 asn≧gly
108 asn≧arg
108 asn≧glu

TABLE 3

Oxygen Affinity Values for Mutant Hemoglobins

| Hemoglobin Mutant | $P_{50}$(mmHg) | $P_{50}$ mutant/$P_{50}$ wild type |
|---|---|---|
| Hgb(beta phe$^{63}$) | 36.0 | 7.5 |
| Hgb(beta ile$^{67}$) | 9.4 | 2.0 |
| Hgb(beta thr$^{102}$) | 11.1 | 4.6 |

TABLE 4

Amino Acid Sequence and Helical Residue Notation for Human Hemoglobin A$_o$

| Helix* | α | Helix* | α | Helix* | β | Helix* | β |
|---|---|---|---|---|---|---|---|
| NA1 | 1 Val | E18 | 69 Ala | NA1 | 1 Val | E18 | 74 Gly |
|  |  | E19 | 70 Val | NA2 | 2 His | E19 | 75 Leu |
| NA2 | 2 Leu | E20 | 71 Ala | NA3 | 3 Leu | E20 | 76 Ala |
| A1 | 3 Ser | EF1 | 72 His | A1 | 4 Thr | EF1 | 77 His |
| A2 | 4 Pro | EF2 | 73 Val | A2 | 5 Pro | EF2 | 78 Leu |
| A3 | 5 Ala | EF3 | 74 Asp | A3 | 6 Glu | EF3 | 79 Asp |
| A4 | 6 Asp | EF4 | 75 Asp | A4 | 7 Glu | EF4 | 80 Asn |
| A5 | 7 Lys | EF5 | 76 Met | A5 | 8 Lys | EF5 | 81 Leu |
| A6 | 8 Thr | EF6 | 77 Pro | A6 | 9 Ser | EF6 | 82 Lys |
| A7 | 9 Asn | EF7 | 78 Asn | A7 | 10 Ala | EF7 | 83 Gly |
| A8 | 10 Val | EF8 | 79 Ala | A8 | 11 Val | EF8 | 84 Thr |
| A9 | 11 Lys | F1 | 80 Leu | A9 | 12 Thr | F1 | 85 Phe |
| A10 | 12 Ala | F2 | 81 Ser | A10 | 13 Ala | F2 | 86 Ala |
| A11 | 13 Ala | F3 | 82 Ala | A11 | 14 Leu | F3 | 87 Thr |
| A12 | 14 Trp | F4 | 83 Leu | A12 | 15 Trp | F4 | 88 Leu |
| A13 | 15 Gly | F5 | 84 Ser | A13 | 16 Gly | F5 | 89 Ser |
| A14 | 16 Lys | F6 | 85 Asp | A14 | 17 Lys | F4 | 90 Glu |
| A15 | 17 Val | F7 | 86 Leu | A15 | 18 Val | F7 | 91 Leu |
| A16 | 18 Gly | F8 | 87 His |  |  | F8 | 92 His |
| AB1 | 19 Ala | F9 | 88 Ala |  |  | F9 | 93 Cys |
| B1 | 20 His | FG1 | 89 His | B1 | 19 Asn | FG1 | 94 Asp |
| B2 | 21 Ala | FG2 | 90 Lys | B2 | 20 Val | FG2 | 95 Lys |
| B3 | 22 Gly | FG3 | 91 Leu | B3 | 21 Asp | FG3 | 96 Leu |
| B4 | 23 Glu | FG4 | 92 Arg | B4 | 22 Glu | FG4 | 97 His |
| B5 | 24 Tyr | FG5 | 93 Val | B5 | 23 Val | FG5 | 98 Val |
| B6 | 25 Gly | G1 | 94 Asp | B6 | 24 Gly | G1 | 99 Asp |
| B7 | 26 Ala | G2 | 95 Pro | B7 | 25 Gly | G2 | 100 Pro |
| B8 | 27 Glu | G3 | 96 Val | B8 | 26 Glu | G3 | 101 Glu |
| B9 | 28 Ala | G4 | 97 Asp | B9 | 27 Ala | G4 | 102 Asn |
| B10 | 29 Leu | G5 | 98 Phe | B10 | 28 Leu | G5 | 103 Phe |
| B11 | 30 Glu | G6 | 99 Lys | B11 | 29 Gly | G6 | 104 Arg |
| B12 | 31 Arg | G7 | 100 Leu | B12 | 30 Arg | G7 | 105 Leu |
| B13 | 32 Met | G8 | 101 Leu | B13 | 31 Leu | G8 | 106 Leu |

TABLE 4-continued

Amino Acid Sequence and Helical Residue Notation for Human Hemoglobin A.

| Helix* | α | Helix* | α | Helix* | β | Helix* | β |
|---|---|---|---|---|---|---|---|
| B14 | 33 Phe | G9 | 102 Ser | B14 | 32 Leu | G9 | 107 Gly |
| B15 | 34 Leu | G10 | 103 His | B15 | 33 Val | G10 | 108 Asn |
| B16 | 35 Ser | G11 | 104 Cys | B16 | 34 Val | G11 | 109 Val |
| C1 | 36 Phe | G12 | 105 Leu | C1 | 35 Tyr | G12 | 110 Leu |
| C2 | 37 Pro | G13 | 106 Leu | C2 | 36 Pro | G13 | 111 Val |
| C3 | 38 Thr | G14 | 107 Val | C3 | 37 Trp | G14 | 112 Cys |
| C4 | 39 Thr | G15 | 108 Thr | C4 | 38 Thr | G15 | 113 Val |
| C5 | 40 Lys | G16 | 109 Leu | C5 | 39 Gln | G16 | 114 Leu |
| C6 | 41 Thr | G17 | 110 Ala | C6 | 40 Arg | G17 | 115 Ala |
| C7 | 42 Tyr | G18 | 111 Ala | C7 | 41 Phe | G18 | 116 His |
| CE1 | 43 Phe | G19 | 112 His | CD1 | 42 Phe | G19 | 117 His |
| CE2 | 44 Pro | GH1 | 113 Leu | CD2 | 43 Glu | GH1 | 118 Phe |
| CE3 | 45 His | GH2 | 114 Pro | CD3 | 44 Ser | GH2 | 119 Gly |
| CE4 | 46 Phe | GH3 | 115 Ala | CD4 | 45 Phe | GH3 | 120 Lys |
|  |  | GH4 | 116 Glu | CD5 | 46 Gly | GH4 | 121 Glu |
| CE5 | 47 Asp | GH5 | 117 Phe | CD6 | 47 Asp | GH5 | 122 Phe |
| CE6 | 48 Leu | H1 | 118 Thr | CD7 | 48 Leu | H1 | 123 Thr |
| CE7 | 49 Ser | H2 | 119 Pro | CD8 | 49 Ser | H2 | 124 Pro |
| CE8 | 50 His | H3 | 120 Ala | D1 | 50 Thr | H3 | 125 Pro |
|  |  | H4 | 121 Val | D2 | 51 Pro | H4 | 126 Val |
|  |  | H5 | 122 His | D3 | 52 Asp | H5 | 127 Gln |
|  |  | H6 | 123 Ala | D4 | 53 Ala | H6 | 128 Ala |
|  |  | H7 | 124 Ser | D5 | 54 Val | H7 | 129 Ala |
|  |  | H8 | 125 Leu | D6 | 55 Met | H8 | 130 Tyr |
| CE9 | 51 Gly | H9 | 126 Asp | D7 | 56 Gly | H9 | 131 Gln |
| E1 | 52 Ser | H10 | 127 Lys | E1 | 57 Asn | H10 | 132 Lys |
| E2 | 53 Ala | H11 | 128 Phe | E2 | 58 Pro | H11 | 133 Val |
| E3 | 54 Gln | H12 | 129 Leu | E3 | 59 Lys | H12 | 134 Val |
| E4 | 55 Val | H13 | 130 Ala | E4 | 60 Val | H13 | 135 Ala |
| E5 | 56 Lys | H14 | 131 Ser | E5 | 61 Lys | H14 | 136 Gly |
| E6 | 57 Gly | H15 | 132 Val | E6 | 62 Ala | H15 | 137 Val |
| E7 | 58 His | H16 | 133 Ser | E7 | 63 His | H16 | 138 Ala |
| E8 | 59 Gly | H17 | 134 Thr | E8 | 64 Gly | H17 | 139 Asn |
| E9 | 60 Lys | H18 | 135 Val | E9 | 65 Lys | H18 | 140 Ala |
| E10 | 61 Lys | H19 | 136 Leu | E10 | 66 Lys | H19 | 141 Leu |
| E11 | 62 Val | H20 | 137 Thr | E11 | 67 Val | H20 | 142 Ala |
| E12 | 63 Ala | H21 | 138 Ser | E12 | 68 Leu | H21 | 143 His |
| E13 | 64 Asp | HC1 | 139 Lys | E13 | 69 Gly | HC1 | 144 Lys |
| E14 | 65 Ala | HC2 | 140 Tyr | E14 | 70 Ala | HC2 | 145 Tyr |
| E15 | 66 Leu | HC3 | 141 Arg | E15 | 71 Phe | HC3 | 146 His |
| E16 | 67 Thr |  |  | E16 | 72 Ser |  |  |
| E17 | 68 Asn |  |  | E17 | 73 Asp |  |  |

TABLE 5

OLIGONUCLEOTIDES USED TO MUTAGENIZE THE ALPHA AND BETA GENES

| Name | Sequence (5' — 3') |
|---|---|
| 94α Sense (SEQUENCE ID: 21) | 5' CGCGTTGTCTGCTCTGTCTGATCTGCACGCTCACAAAC TGCGTGTTTGCCCGGTT 3' |
| 94α Antisense (SEQUENCE ID: 22) | 5' AACCGGGCAAACACGCAGTTTGTGAGCGTGCAGATCAGA CAGAGCAGACAA 3' |
| 97β Sense (SEQUENCE ID: 23) | 5' CCACTGCGACAAACTGTCCGTTGACCCGGAAAACTTCCG TCTGCTGGGTAACGTA 3' |
| 97β Antisense (SEQUENCE ID: 24) | 5' CTAGTACGTTACCCAGCAGACGGAAGTTTTCCGGGTCAA CGCACAGTTTGTCGCAGTGGAGCT |
| 99β Sense (SEQUENCE ID: 25) | 5' CCACTGCGACAAACTGCACGTTTGCCCGGAAAACTTCCG TCTGCTGGGTAACGTA 3' |
| 99β Antisense (SEQUENCE ID: 26) | 5' CTAGTACGTTACCCAGCAGACGGAAGTTTTCCGGGCAAA CGTGCAGTTTGTCGCAGTGGAGCT 3' |
| 101β Sense (SEQUENCE ID: 27) | 5' CCACTGCGACAAACTGCACGTTTGACCCGTGCAACTTCCG TCTGCTGGGTAACGTA 3' |
| 101β Antisense (SEQUENCE ID: 28) | 5' CTAGTACGTTACCCAGCAGTCGGAAGTTGCACGGGTCAA CGTGCAGTTTGTCGCAGTGGAGCT 3' |

TABLE 6

PRIMERS USED FOR THE SEQUENCING OF α AND β GENES

| Name | Length | Sequence (5' — 3') |
|---|---|---|
| Universal Primer (SEQUENCE ID: 29) | 17 mer | GTAAAACGACGGCCAGT |
| Reverse Universal Primer (SEQUENCE ID: 30) | 16 mer | AACAGCTATGACCATG |
| Primer no. 2 (SEQUENCE ID: 31) | 18 mer | TGGCTTCTGTTTCTACCG |
| Primer No. 3 (SEQUENCE ID: 32) | 18 mer | TTTCTCTCACGGTCTGGC |
| Reverse Primer No. 2 (SEQUENCE ID: 33) | 18 mer | CAGACCGTCAGAGAAAGC |
| Reverse Primer No. 3 (SEQUENCE ID: 34) | 18 mer | GTAGAAACAGAAGCCAGG |

---

We claim:

1. A blood substitute comprising a recombinantly-produced mutant hemoglobin and having an osmolarity greater than 303 milliosmoles per liter.

2. The blood substitute of claim 1 having an osmolarity in the range of 500–800 milliosmoles per liter.

3. The blood substitute of claim 2 having an osmolarity in the range of 600–800 milliosmoles per liter.

4. The blood substitute of claim 1 comprising a red blood cell free mutant hemoglobin and a disaccharide.

5. A hyperosmolar blood substitute comprising a recombinantly-produced mutant hemoglobin oxygen carrier and a physiologically acceptable molecule that is less diffusible than dextrose, wherein said substitute has an osmolarity greater than 303 milliosmoles per liter.

6. The blood substitute of claim 5 wherein said molecule less diffusible than dextrose is a disaccharide.

7. The blood substitute of claim 6 wherein the disaccharide is sucrose.

8. A hyperosmolar blood substitute composition having an osmolarity greater than that of protein free blood and less than 800 milliosmoles per liter comprising:

(a) a physiologically acceptable fluid electrolyte solution;

(b) a physiologically acceptable agent capable of increasing the osmolarity of said blood substitute to a value greater than that of protein free blood and less than 800 milliosmoles per liter;

(c) a recombinantly produced mutant hemoglobin oxygen carrying substance; and (d) a sufficient amount of water to achieve the desired osmolarity.

9. A hyperosmolar blood substitute solution having an osmolarity in the range of 500 to 800 milliosmoles per liter comprising:

(a) physiologically acceptable electrolytes;

(b) a physiologically acceptable agent wherein said physiologically acceptable agent increases the osmolarity of said solution to a value in the range of 500 to 800 milliosmoles per liter; and (c) an oxygen carrying red blood cell free mutant hemoglobin.

10. A blood substitute comprising:

(a) a hyperosmolar solution and (b) an oxygen carrying recombinantly produced mutant hemoglobin.

* * * * *

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
        ( A ) LENGTH: 141
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Val Leu Ser Pro Ala Asp Lys Thr Asn Val Lys Ala Ala Trp Gly
                  5                  10                  15
Lys Val Gly Ala His Ala Gly Glu Tyr Gly Ala Glu Ala Leu Glu
                 20                  25                  30
Arg Met Phe Leu Ser Phe Pro Thr Thr Lys Thr Tyr Phe Pro His
                 35                  40                  45
Phe Asp Leu Ser His Gly Ser Ala Gln Val Lys Gly His Gly Lys
                 50                  55                  60
Lys Val Ala Asp Ala Leu Thr Asn Ala Val Ala His Val Asp Asp
                 65                  70                  75
Met Pro Asn Ala Leu Ser Ala Leu Ser Asp Leu His Ala His Lys
                 80                  85                  90
Leu Arg Val Asp Pro Val Asn Phe Lys Leu Leu Ser His Cys Leu
                 95                 100                 105
Leu Val Thr Leu Ala Ala His Leu Pro Ala Glu Phe Thr Pro Ala
                110                 115                 120
Val His Ala Ser Leu Asp Lys Phe Leu Ala Ser Val Ser Thr Val
                125                 130                 135
Leu Thr Ser Lys Tyr Arg
                140
```

( 2 ) INFORMATION FOR SEQ ID NO:2:

( i ) SEQUENCE CHARACTERISTICS:
        ( A ) LENGTH: 146
        ( B ) TYPE: amino acid
        ( D ) TOPOLOGY: unknown to applicant ( i i ) MOLECULE TYPE: protein (iii) HYPOTHETICAL: no (xi) SEQUENCE DESCRIPTION: SEQ ID NO:2:

| Val | His | Leu | Thr | Pro | Glu | Glu | Lys | Ser | Ala | Val | Thr | Ala | Leu | Trp |
|---|---|---|---|---|---|---|---|---|---|---|---|---|---|---|
| | | | | 5 | | | | 10 | | | | | | 15 |
| Gly | Lys | Val | Asn | Val | Asp | Glu | Val | Gly | Gly | Glu | Ala | Leu | Gly | Arg |
| | | | | 20 | | | | 25 | | | | | | 30 |
| Leu | Leu | Val | Val | Tyr | Pro | Trp | Thr | Gln | Arg | Phe | Phe | Glu | Ser | Phe |
| | | | | 35 | | | | 40 | | | | | | 45 |
| Gly | Asp | Leu | Ser | Thr | Pro | Asp | Ala | Val | Met | Gly | Asn | Pro | Lys | Val |
| | | | | 50 | | | | 55 | | | | | | 60 |
| Lys | Ala | His | Gly | Lys | Lys | Val | Leu | Gly | Ala | Phe | Ser | Asp | Gly | Leu |
| | | | | 65 | | | | 70 | | | | | | 75 |
| Ala | His | Leu | Asp | Asn | Leu | Lys | Gly | Thr | Phe | Ala | Thr | Leu | Ser | Glu |
| | | | | 80 | | | | 85 | | | | | | 90 |
| Leu | His | Cys | Asp | Lys | Leu | His | Val | Asp | Pro | Glu | Asn | Phe | Arg | Leu |
| | | | | 95 | | | | 100 | | | | | | 105 |
| Leu | Gly | Asn | Val | Leu | Val | Cys | Val | Leu | Ala | His | His | Phe | Gly | Lys |
| | | | | 110 | | | | 115 | | | | | | 120 |
| Glu | Phe | Thr | Pro | Pro | Val | Gln | Ala | Ala | Tyr | Gln | Lys | Val | Val | Ala |
| | | | | 125 | | | | 130 | | | | | | 135 |
| Gly | Val | Ala | Asn | Ala | Leu | Ala | His | Lys | Tyr | His | | | | |
| | | | | 140 | | | | 145 | | | | | | |

(2) INFORMATION FOR SEQ ID NO:3:

(i) SEQUENCE CHARACTERISTICS:
        (A) LENGTH: 423
        (B) TYPE: nucleic acid
        (C) STRANDEDNESS: single
        (D) TOPOLOGY: unknown to applicant (ii) MOLECULE TYPE: Other nucleic acid
        (A) DESCRIPTION: Human alpha globin sequence (iii) HYPOTHETICAL: no (xi) SEQUENCE DESCRIPTION: SEQ ID NO:3:

```
GTGCTGTCTC  CTGCCGACAA  GACCAACGTC  AAGGCCGCCT  GGGGCAAGGT   50
TGGCGCGCAC  GCTGGCGAGT  ATGGTGCGGA  GGCCCTGGAG  AGGATGTTCC  100
TGTCCTTCCC  CACCACCAAG  ACCTACTTCC  CGCACTTCGA  CCTGAGCCAC  150
GGCTCTGCCC  AGGTTAAGGG  CCACGGCAAG  AAGGTGGCCG  ACGCGCTGAC  200
CAACGCCGTG  GCGCACGTGG  ACGACATGCC  CAACGCGCTG  TCCGCCCTGA  250
GCGACCTGCA  CGCGCACAAG  CTTCGGGTGG  ACCCGGTCAA  CTTCAAGCTC  300
CTAAGCCACT  GCCTGCTGGT  GACCCTGGCC  GCCCACCTCC  CCGCCGAGTT  350
CACCCCTGCG  GTGCACGCCT  CCCTGGACAA  GTTCCTGGCT  TCTGTGAGCA  400
CCGTGCTGAC  CTCCAAATAC  CGT                                 423
```

(2) INFORMATION FOR SEQ ID NO:4:

(i) SEQUENCE CHARACTERISTICS:
        (A) LENGTH: 438
        (B) TYPE: nucleic acid
        (C) STRANDEDNESS: single
        (D) TOPOLOGY: unknown to applicant (ii) MOLECULE TYPE: Other nucleic acid
        (A) DESCRIPTION: Human beta globin sequence (iii) HYPOTHETICAL: no (xi) SEQUENCE DESCRIPTION: SEQ ID NO:4:

| | | | | |
|---|---|---|---|---|
| GTGCACCTGA | CTCCTGAGGA | GAAGTCTGCC | GTTACTGCCC | TGTGGGGCAA 50 |
| GGTGAACGTG | GATGAAGTTG | GTGGTGAGGC | CCTGGGCAGG | CTGCTGGTGG 100 |
| TCTACCCTTG | GACCCAGAGG | TTCTTTGAGT | CCTTTGGGGA | TCTGTCCACT 150 |
| CCTGATGCTG | TTATGGGCAA | CCCTAAGGTG | AAGGCTCATG | GCAAGAAAGT 200 |
| GCTCGGTGCC | TTTAGTGATG | GCCTGGCTCA | CCTGGACAAC | CTCAAGGGCA 250 |
| CCTTTGCCAC | ACTGAGTGAG | CTGCACTGTG | ACAAGCTGCA | CGTGGATCCT 300 |
| GAGAACTTCA | GGCTCCTGGG | CAACGTGCTG | GTCTGTGTGC | TGGCCCATCA 350 |
| CTTTGGCAAA | GAATTCACCC | CACCAGTGCA | GGCTGCCTAT | CAGAAAGTGG 400 |
| TGGCTGGTGT | GGCTAATGCC | CTGGCCCACA | AGTATCAC | 438 |

(2) INFORMATION FOR SEQ ID NO:5:

(i) SEQUENCE CHARACTERISTICS:
        (A) LENGTH: 36
        (B) TYPE: nucleic acid
        (C) STRANDEDNESS: single
        (D) TOPOLOGY: unknown to applicant (ii) MOLECULE TYPE: Other nucleic acid
        (A) DESCRIPTION: ARTIFICIALLY GENERATED
            OLIGONUCLEOTIDE USED IN A CLONING VECTOR (iii) HYPOTHETICAL: no (xi) SEQUENCE DESCRIPTION: SEQ ID NO:5:

GGATCCATCC GAGGGTAGGC CTACCCTCGA TGGATC 36

(2) INFORMATION FOR SEQ ID NO:6:

(i) SEQUENCE CHARACTERISTICS:
        (A) LENGTH: 11
        (B) TYPE: amino acid
        (D) TOPOLOGY: unknown to applicant (ii) MOLECULE TYPE: peptide (iii) HYPOTHETICAL: no (xi) SEQUENCE DESCRIPTION: SEQ ID NO:6:

Gly Ser Ile Glu Gly Arg Arg Gly Glu Ile Ser
1               5                   10

(2) INFORMATION FOR SEQ ID NO:7:

(i) SEQUENCE CHARACTERISTICS:
        (A) LENGTH: 30
        (B) TYPE: nucleic acid
        (C) STRANDEDNESS: single
        (D) TOPOLOGY: unknown to applicant (ii) MOLECULE TYPE: Other nucleic acid
        (A) DESCRIPTION: ARTIFICIALLY GENERATED
            OLIGONUCLEOTIDE USED IN A CLONING VECTOR (iii) HYPOTHETICAL: no (xi) SEQUENCE DESCRIPTION: SEQ ID NO:7:

ACAGCGGAAG GGGGATCCAT GGTGCACCTG 30

(2) INFORMATION FOR SEQ ID NO:8:

( i ) SEQUENCE CHARACTERISTICS:
    ( A ) LENGTH: 10
    ( B ) TYPE: amino acid
    ( D ) TOPOLOGY: unknown to applicant ( i i ) MOLECULE TYPE: peptide ( i i i ) HYPOTHETICAL: no ( x i ) SEQUENCE DESCRIPTION: SEQ ID NO:8:

Thr Ala Glu Gly Gly Ser Met Val His Leu
 1               5                   10

( 2 ) INFORMATION FOR SEQ ID NO:9:

( i ) SEQUENCE CHARACTERISTICS:
        ( A ) LENGTH: 39
        ( B ) TYPE: nucleic acid
        ( C ) STRANDEDNESS: single
        ( D ) TOPOLOGY: unknown to applicant ( i i ) MOLECULE TYPE: Other nucleic acid
        ( A ) DESCRIPTION: ARTIFICIALLY GENERATED
            OLIGONUCLEOTIDE USED IN A CLONING VECTOR ( i i i ) HYPOTHETICAL: no ( x i ) SEQUENCE DESCRIPTION: SEQ ID NO:9:

ACAGCGGAAG GGGGATCCAT CGAGGGTAGG GTGCACCTG    39

( 2 ) INFORMATION FOR SEQ ID NO:10:

( i ) SEQUENCE CHARACTERISTICS:
        ( A ) LENGTH: 13
        ( B ) TYPE: amino acid
        ( D ) TOPOLOGY: unknown to applicant ( i i ) MOLECULE TYPE: peptide ( i i i ) HYPOTHETICAL: yes ( x i ) SEQUENCE DESCRIPTION: SEQ ID NO:10:

Thr Ala Glu Gly Gly Ser Ile Glu Gly Arg Val His Leu
 1               5                   10

( 2 ) INFORMATION FOR SEQ ID NO:11:

( i ) SEQUENCE CHARACTERISTICS:
        ( A ) LENGTH: 10
        ( B ) TYPE: nucleic acid
        ( C ) STRANDEDNESS: single
        ( D ) TOPOLOGY: unknown to applicant ( i i ) MOLECULE TYPE: Other nucleic acid
        ( A ) DESCRIPTION: ARTIFICIALLY GENERATED
            OLIGONUCLEOTIDE USED IN A CLONING VECTOR ( i i i ) HYPOTHETICAL: no ( x i ) SEQUENCE DESCRIPTION: SEQ ID NO:11:

CACCATGGTG    10

( 2 ) INFORMATION FOR SEQ ID NO:12:

( i ) SEQUENCE CHARACTERISTICS:
        ( A ) LENGTH: 10
        ( B ) TYPE: nucleic acid
        ( C ) STRANDEDNESS: single
        ( D ) TOPOLOGY: unknown to applicant ( i i ) MOLECULE TYPE: Other nucleic acid (A) DESCRIPTION: ARTIFICIALLY GENERATED OLIGONUCLEOTIDE
USED IN A CLONING VECTOR (iii) HYPOTHETICAL: no (xi) SEQUENCE DESCRIPTION: SEQ ID NO:12:

AACGGGCCCT 10

(2) INFORMATION FOR SEQ ID NO:13:

(i) SEQUENCE CHARACTERISTICS:
(A) LENGTH: 15
(B) TYPE: nucleic acid
(C) STRANDEDNESS: single
(D) TOPOLOGY: unknown to applicant (ii) MOLECULE TYPE: Other nucleic acid
(A) DESCRIPTION: ARTIFICIALLY GENERATED OLIGONUCLEOTIDE
USED IN A CLONING VECTOR (iii) HYPOTHETICAL: no (xi) SEQUENCE DESCRIPTION: SEQ ID NO:13:

TACCCTCGAT GGATC 15

(2) INFORMATION FOR SEQ ID NO:14:

(i) SEQUENCE CHARACTERISTICS:
(A) LENGTH: 15
(B) TYPE: nucleic acid
(C) STRANDEDNESS: single
(D) TOPOLOGY: unknown to applicant (ii) MOLECULE TYPE: Other nucleic acid
(A) DESCRIPTION: ARTIFICIALLY GENERATED
OLIGONUCLEOTIDE USED IN A CLONING VECTOR (iii) HYPOTHETICAL: no (xi) SEQUENCE DESCRIPTION: SEQ ID NO:14:

CATCGAGGGT AGGCC 15

(2) INFORMATION FOR SEQ ID NO:15:

(i) SEQUENCE CHARACTERISTICS:
(A) LENGTH: 6
(B) TYPE: amino acid
(D) TOPOLOGY: unknown to applicant (ii) MOLECULE TYPE: peptide (iii) HYPOTHETICAL: no (xi) SEQUENCE DESCRIPTION: SEQ ID NO:15:

Gly Ser Ile Glu Gly Arg
1               5

(2) INFORMATION FOR SEQ ID NO:16:

(i) SEQUENCE CHARACTERISTICS:
(A) LENGTH: 4
(B) TYPE: amino acid
(D) TOPOLOGY: unknown to applicant (ii) MOLECULE TYPE: peptide (iii) HYPOTHETICAL: no (xi) SEQUENCE DESCRIPTION: SEQ ID NO:16:

Ile Glu Gly Arg
1

( 2 ) INFORMATION FOR SEQ ID NO:17:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: unknown to applicant ( i i ) MOLECULE TYPE: Other nucleic acid
        ( A ) DESCRIPTION: ARTIFICIALLY GENERATED
            OLIGONUCLEOTIDE USED IN A CLONING VECTOR ( i i i ) HYPOTHETICAL: no ( x i ) SEQUENCE DESCRIPTION: SEQ ID NO:17:

ACCAACTTCA GATCTGTTAC CTTG    24

( 2 ) INFORMATION FOR SEQ ID NO:18:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: unknown to applicant ( i i ) MOLECULE TYPE: Other nucleic acid
        ( A ) DESCRIPTION: ARTIFICIALLY GENERATED
            OLIGONUCLEOTIDE USED IN A CLONING VECTOR ( i i i ) HYPOTHETICAL: no ( x i ) SEQUENCE DESCRIPTION: SEQ ID NO:18:

GGAGCCTGAA GTTCTCAGGA    20

( 2 ) INFORMATION FOR SEQ ID NO:19:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: unknown to applicant ( i i ) MOLECULE TYPE: Other nucleic acid
        ( A ) DESCRIPTION: ARTIFICIALLY GENERATED
            OLIGONUCLEOTIDE USED IN A CLONING VECTOR ( i i i ) HYPOTHETICAL: no ( x i ) SEQUENCE DESCRIPTION: SEQ ID NO:19:

GCACCGAGGA TTTTCTTGCC    20

( 2 ) INFORMATION FOR SEQ ID NO:20:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: unknown to applicant ( i i ) MOLECULE TYPE: Other nucleic acid
        ( A ) DESCRIPTION: ARTIFICIALLY GENERATED
            OLIGONUCLEOTIDE USED IN A CLONING VECTOR ( i i i ) HYPOTHETICAL: no ( x i ) SEQUENCE DESCRIPTION: SEQ ID NO:20:

TTCTTGCCGA AAGCCTTCCA    20

( 2 ) INFORMATION FOR SEQ ID NO:21:

( i ) SEQUENCE CHARACTERISTICS:
  ( A ) LENGTH: 55
  ( B ) TYPE: nucleic acid
  ( C ) STRANDEDNESS: single
  ( D ) TOPOLOGY: unknown to applicant ( i i ) MOLECULE TYPE: Other nucleic acid
  ( A ) DESCRIPTION: mutagenizing oligonucleotide ( i i i ) HYPOTHETICAL: no ( i v ) ANTI-SENSE: no ( x i ) SEQUENCE DESCRIPTION: SEQ ID NO:21:

CGCGTTGTCT GCTCTGTCTG ATCTGCACGC TCACAAACTG 40

CGTGTTTGCC CGGTT 55

( 2 ) INFORMATION FOR SEQ ID NO:22:

( i ) SEQUENCE CHARACTERISTICS:
    ( A ) LENGTH: 51
    ( B ) TYPE: nucleic acid
    ( C ) STRANDEDNESS: single
    ( D ) TOPOLOGY: unknown to applicant ( i i ) MOLECULE TYPE: Other nucleic acid
    ( A ) DESCRIPTION: mutagenizing oligonucleotide ( i i i ) HYPOTHETICAL: no ( i v ) ANTI-SENSE: yes ( x i ) SEQUENCE DESCRIPTION: SEQ ID NO:22:

AACCGGGCAA ACACGCAGTT TGTGAGCGTG CAGATCAGAC 40

AGAGCAGACA A 51

( 2 ) INFORMATION FOR SEQ ID NO:23:

( i ) SEQUENCE CHARACTERISTICS:
    ( A ) LENGTH: 55
    ( B ) TYPE: nucleic acid
    ( C ) STRANDEDNESS: single
    ( D ) TOPOLOGY: unknown to applicant ( i i ) MOLECULE TYPE: Other nucleic acid
    ( A ) DESCRIPTION: mutagenizing oligonucleotide ( i i i ) HYPOTHETICAL: no ( i v ) ANTI-SENSE: no ( x i ) SEQUENCE DESCRIPTION: SEQ ID NO:23:

CCACTGCGAC AAACTGTGCG TTGACCCGGA AAACTTCCGT 40

CTGCTGGGTA ACGTA 55

( 2 ) INFORMATION FOR SEQ ID NO:24:

( i ) SEQUENCE CHARACTERISTICS:
    ( A ) LENGTH: 63
    ( B ) TYPE: nucleic acid
    ( C ) STRANDEDNESS: single
    ( D ) TOPOLOGY: unknown to applicant ( i i ) MOLECULE TYPE: Other nucleic acid
    ( A ) DESCRIPTION: mutagenizing oligonucleotide ( i i i ) HYPOTHETICAL: no ( i v ) ANTI-SENSE: yes ( x i ) SEQUENCE DESCRIPTION: SEQ ID NO:24:

```
CTAGTACGTT ACCCAGCAGA CGGAAGTTTT CCGGGTCAAC    40

GCACAGTTTG TCGCAGTGGA GCT    63
```

( 2 ) INFORMATION FOR SEQ ID NO:25:

( i ) SEQUENCE CHARACTERISTICS:
        ( A ) LENGTH: 55
        ( B ) TYPE: nucleic acid
        ( C ) STRANDEDNESS: single
        ( D ) TOPOLOGY: unknown to applicant ( i i ) MOLECULE TYPE: Other nucleic acid
        ( A ) DESCRIPTION: mutagenizing oligonucleotide ( i i i ) HYPOTHETICAL: no ( i v ) ANTI-SENSE: no ( x i ) SEQUENCE DESCRIPTION: SEQ ID NO:25:

```
CCACTGCGAC AAACTGCACG TTTGCCCGGA AAACTTCCGT    40

CTGCTGGGTA ACGTA    55
```

( 2 ) INFORMATION FOR SEQ ID NO:26:

( i ) SEQUENCE CHARACTERISTICS:
        ( A ) LENGTH: 62
        ( B ) TYPE: nucleic acid
        ( C ) STRANDEDNESS: single
        ( D ) TOPOLOGY: unknown to applicant ( i i ) MOLECULE TYPE: Other nucleic acid
        ( A ) DESCRIPTION: mutagenizing oligonucleotide ( i i i ) HYPOTHETICAL: no ( i v ) ANTI-SENSE: yes ( x i ) SEQUENCE DESCRIPTION: SEQ ID NO:26:

```
CTAGTACGTT ACCCAGCAGA CGGAAGTTTT CCGGGCAAAC    40

GTGCATTTGT CGCAGTGGAG CT    62
```

( 2 ) INFORMATION FOR SEQ ID NO:27:

( i ) SEQUENCE CHARACTERISTICS:
        ( A ) LENGTH: 55
        ( B ) TYPE: nucleic acid
        ( C ) STRANDEDNESS: single
        ( D ) TOPOLOGY: unknown to applicant ( i i ) MOLECULE TYPE: Other nucleic acid
        ( A ) DESCRIPTION: mutagenizing oligonucleotide ( i i i ) HYPOTHETICAL: no ( i v ) ANTI-SENSE: no ( x i ) SEQUENCE DESCRIPTION: SEQ ID NO:27:

```
CCACTGCGAC AAACTGCACG TTGACCCGTG CAACTTCCGT    40

CTGCTGGGTA ACGTA    55
```

( 2 ) INFORMATION FOR SEQ ID NO:28:

( i ) SEQUENCE CHARACTERISTICS:
        ( A ) LENGTH: 63
        ( B ) TYPE: nucleic acid
        ( C ) STRANDEDNESS: single
        ( D ) TOPOLOGY: unknown to applicant (i i) MOLECULE TYPE: Other nucleic acid
(A) DESCRIPTION: mutagenizing oligonucleotide (i i i) HYPOTHETICAL: no (i v) ANTI-SENSE: yes (x i) SEQUENCE DESCRIPTION: SEQ ID NO:28:

CTAGTACGTT ACCCAGCAGT CGGAAGTTGC ACGGGTCAAC 40

GTGCAGTTTG TCGCAGTGGA GCT 63

(2) INFORMATION FOR SEQ ID NO:29:

(i) SEQUENCE CHARACTERISTICS:
(A) LENGTH: 17
(B) TYPE: nucleic acid
(C) STRANDEDNESS: single
(D) TOPOLOGY: unknown to applicant (i i) MOLECULE TYPE: Other nucleic acid
(A) DESCRIPTION: universal sequencing primer (i i i) HYPOTHETICAL: no (x i) SEQUENCE DESCRIPTION: SEQ ID NO:29:

GTAAAACGAC GGCCAGT 17

(2) INFORMATION FOR SEQ ID NO:30:

(i) SEQUENCE CHARACTERISTICS:
(A) LENGTH: 16
(B) TYPE: nucleic acid
(C) STRANDEDNESS: single
(D) TOPOLOGY: unknown to applicant (i i) MOLECULE TYPE: Other nucleic acid
(A) DESCRIPTION: primer (i i i) HYPOTHETICAL: no (x i) SEQUENCE DESCRIPTION: SEQ ID NO:30:

AACAGCTATG ACCATG 16

(2) INFORMATION FOR SEQ ID NO:31:

(i) SEQUENCE CHARACTERISTICS:
(A) LENGTH: 18
(B) TYPE: nucleic acid
(C) STRANDEDNESS: single
(D) TOPOLOGY: unknown to applicant (i i) MOLECULE TYPE: Other nucleic acid
(A) DESCRIPTION: primer (i i i) HYPOTHETICAL: no (x i) SEQUENCE DESCRIPTION: SEQ ID NO:31:

TGGCTTCTGT TTCTACCG 18

(2) INFORMATION FOR SEQ ID NO:32:

(i) SEQUENCE CHARACTERISTICS:
(A) LENGTH: 18
(B) TYPE: nucleic acid
(C) STRANDEDNESS: single
(D) TOPOLOGY: unknown to applicant (i i) MOLECULE TYPE: Other nucleic acid
(A) DESCRIPTION: primer (i i i) HYPOTHETICAL: no ( x i ) SEQUENCE DESCRIPTION: SEQ ID NO:32:

TTTCTCTGAC GGTCTGGC 18

( 2 ) INFORMATION FOR SEQ ID NO:33:

( i ) SEQUENCE CHARACTERISTICS:
( A ) LENGTH: 18
( B ) TYPE: nucleic acid
( C ) STRANDEDNESS: single
( D ) TOPOLOGY: unknown to applicant ( i i ) MOLECULE TYPE: Other nucleic acid
( A ) DESCRIPTION: primer ( i i i ) HYPOTHETICAL: no ( x i ) SEQUENCE DESCRIPTION: SEQ ID NO:33:

CAGACCGTCA GAGAAAGC 18

( 2 ) INFORMATION FOR SEQ ID NO:34:

( i ) SEQUENCE CHARACTERISTICS:
( A ) LENGTH: 18
( B ) TYPE: nucleic acid
( C ) STRANDEDNESS: single
( D ) TOPOLOGY: unknown to applicant ( i i ) MOLECULE TYPE: Other nucleic acid
( A ) DESCRIPTION: primer ( i i i ) HYPOTHETICAL: no ( x i ) SEQUENCE DESCRIPTION: SEQ ID NO:34:

GTAGAAACAG AAGCCAGG 18